United States Patent
Blasco Marhuenda et al.

(10) Patent No.: US 11,261,434 B2
(45) Date of Patent: Mar. 1, 2022

(54) TELOMERASE REVERSE TRANSCRIPTASE-BASED THERAPIES FOR TREATMENT OF CONDITIONS ASSOCIATED WITH MYOCARDIAL INFARCTION

(71) Applicants: FUNDACIÓN CENTRO NACIONAL DE INVESTIGACIONES ONCÓLOGICAS CARLOSIII, Madrid (ES); UNIVERSITAT AUTÒNOMA DE BARCELONA, Bellaterra (ES)

(72) Inventors: Maria Antonia Blasco Marhuenda, Madrid (ES); Bruno Bernardes De Jesus, Madrid (ES); Christian Baer, Madrid (ES); Rosa María Serrano Ruiz, Madrid (ES); Fàtima Bosch I Tubert, Bellaterra (ES); Eduard Ayuso, Bellaterra (ES); Ivan Formentini, Basel (CH); Maria Bobadilla, Rosenau (FR); Jacques Mizrahi, Bottmingen (CH)

(73) Assignees: Fundación del Sector Público Estatal Centro Nacional de Investigaciones Oncológicas Carlos III (F.S.P. CNIO), Madrid (ES); Universität Autónoma de Barcelona, Bellaterra (ES)

( * ) Notice: Subject to any disclaimer, the term of this patent is extended or adjusted under 35 U.S.C. 154(b) by 296 days.

(21) Appl. No.: 15/502,530

(22) PCT Filed: Aug. 4, 2015

(86) PCT No.: PCT/EP2015/067875
§ 371 (c)(1),
(2) Date: Feb. 8, 2017

(87) PCT Pub. No.: WO2016/020346
PCT Pub. Date: Feb. 11, 2016

(65) Prior Publication Data
US 2017/0191045 A1    Jul. 6, 2017

(30) Foreign Application Priority Data
Aug. 8, 2014   (EP) .................................... 14382311

(51) Int. Cl.
*A61K 48/00*       (2006.01)
*C12N 9/12*        (2006.01)
*A61K 38/45*       (2006.01)

(52) U.S. Cl.
CPC ............ *C12N 9/1276* (2013.01); *A61K 38/45* (2013.01); *A61K 48/005* (2013.01); *C12Y 207/07049* (2013.01); *C12N 2750/14143* (2013.01)

(58) Field of Classification Search
None
See application file for complete search history.

(56) References Cited

U.S. PATENT DOCUMENTS

2015/0322416 A1*  11/2015  Andrews ................ A61K 48/00
                                                    514/44 R

FOREIGN PATENT DOCUMENTS

| EP | 1254952 A1 | 11/2002 |
| EP | 2402038 A1 | 1/2012 |
| WO | 2004/092395 A2 | 10/2004 |
| WO | 2013/169077 A1 | 11/2013 |

OTHER PUBLICATIONS

Bemelmans et al., PLOS One, 2013, 8: 1-9.*
Urbanek et al., Proc. Natl. Acad. Sci. USA, 2005, 102: 8692-8697.*
Anversa et al., Nature, 2002, 415: 240-243.*
Espcenet Bibliographic Data, 2019.*
Sequence Alignment, 2019.*
van Vliet et al., Methods in Molecular Biology, 2008, Chapter 2, p. 51-91.*
Jin et al., Current Pharmaceutical Design, 2004, 10: 2525-2533.*
Mudd, J. O. et al., Tackling Heart Failure in the Twenty-First Century, Nature 451 (2008): 919-928.
Liew, C-C. et al., Molecular Genetics and Genomics of Heart Failure, Nature Reviews, Genetics 5 (2004): 811-825.
Cohn, J. N. et al., Cardiac Remodeling Concepts and Clinical Implications: A Consensus Paper From an International Forum on Cardiac Remodeling, J. Am. Coll. Cardiol. 35, 3 (2000): 569-582.
Dominguez, L. J. et al., Ageing, lifestyle modifications, and cardiovascular disease in developing countries, The Journal of Nutrition, Health & Aging 10 (2006): 143-149.
Bergmann, O. et al., Evidence for Cardiomyocyte Renewal in Humans, Science 324 (2009): 98-102.
Porrello, E. R. et al., Transient Regenerative Potential of the Neonatal Mouse Heart, Science 331 (2011): 1078-1080.
Haubner, B. J. et al., Complete cardiac regeneration in a mouse model of myocardial infarction. Aging (Albany NY) 4 (2012): 966-977.
López-Otín et al.,The Hallmarks of Aging, Cell, Leading Edge Review 153, (2013): 1194-1217.
Boonekamp, J. J. et al.,Telomere length behaves as biomarker of somatic redundancy rather than biological age, Aging Cell 12 (2013): 330-332.
Blackbum, E. H., Switching and Signaling at the Telomere, Cell 106 (2001): 661-673.
de Lange, T., Shelterin: the protein complex that shapes and safeguards human telomeres, Genes Dev 19 (2005).
Greider, C. W. et al., Identification of a Specific Telomere Terminal Transferase Activity in Tetrahymena Extracts, Cell 43 (1985): 405-413.

(Continued)

*Primary Examiner* — Ileana Popa
(74) *Attorney, Agent, or Firm* — N.V. Nederlandsch Octrooibureau; Tamara C. Stegmann; Catherine A. Shultz

(57) ABSTRACT

The invention provides compositions and methods useful for the treatment and prevention of conditions associated with myocardial infarction.

12 Claims, 4 Drawing Sheets

Specification includes a Sequence Listing.

(56) References Cited

OTHER PUBLICATIONS

Vera, E. et al., The Rate of Increase of Short Telomeres Predicts Longevity in Mammals, Cell Reports 2 (2012): 732-737.
Flores, I. et al., The longest telomeres: a general signature of adult stem cell compartments, Genes & Development 22 (2008): 654-667.
Harley, C. B. et al., Telomeres shorten during ageing of human fibroblasts, Nature 345 (1990): 458-460.
Canela, A. et al., High-throughput telomere length quantification by FISH and its application to human population studies. Proc Natl Acad Sci USA 104 (2007): 5300-5305.
Flores, I. et al., Effects of telomerase and telomere length on epidermal stem cell behavior, Science 309 (2005): 1253-1256.
Heidinger, B. J. et al., Telomere length in early life predicts lifespan, Proc Natl Acad Sci USA 109 (2012): 1743-1748.
Leri, A. et al., Ablation of telomerase and telomere loss leads to cardiac dilatation and heart failure associated with p53 upregulation, EMBO J 22 (2003): 131-139.
De Jesus, B. B. et al., Assessing cell and organ senescence biomarkers, Circ Res 111 (2012): 97-109.
De Meyer et al., Telomere length and cardiovascular aging: the means to the ends?, Ageing Research Reviews 10 (2011): 297-303.
Blasco, M. A. et al., Functional characterization and developmental regulation of mouse telomerase RNA, Science 269, (1995): 1267-1270.
Borges, A. et al., Telomerase Activity During Cardiac Development. J Mol Cell Cardiol 29 (1997): 2717-2724.
Tomas-Loba, A. et al., Telomerase Reverse Transcriptase delays Aging in Cancer-Resistant Mice. Cell 135 (2008): 609-622.
Oh, H. et al., Telomerase reverse transcriptase promotes cardiac muscle cell proliferation, hypertrophy, and survival, Proc Natl Acad Sci USA 98 (2001): 10308-10313.
de Jesus, B. et al., Telomerase gene therapy in adult and old mice delays aging and increases longevity without increasing cancer, EMBO Molecular Medicine Med 30(4) (2012): 691-704.
Park, J. I. et al., Telomerase modulates Wnt signalling by association with target gene chromatin, Nature 460 (2009): 66-72.
Gao, G. P. et al., Novel adeno-associated viruses from rhesus monkeys as vectors for human gene therapy, Proc Natl Acad Sci USA 99 (2002): 11854-11859.
Zincarelli, C. et al., Analysis of AAV 3 Serotypes 1-9 Mediated Gene Expression and Tropism in Mice After Systemic Injection. Molecular Therapy 16(6) (2008): 1073-1080.
van den Borne, S. W. et al., Mouse strain determines the outcome of wound healing after myocardial infarction, Cardiovasc Research 84 (2009): 273-282.
Konkalmatt, P. R. et al., Cardiac-Selective Expression of Extracellular Superoxide Dismutase After Systemic Injection of Adeno-Associated Virus 9 Protects the Heart Against Post-Myocardial Infarction Left Ventricular Remodeling, Circ Cardiovasc Imaging 6 (2013): 478-486.
Stegger, L. et al., Accurate Noninvasive Measurement of Infarct Size in Mice with High-Resolution PET, J Nucl Med 47 (2006): 1837-1844.
Ertl, G. et al., Healing after myocardial infarction, Cardiovascular Research 66(14) (2005): 22-32.
Brew, K. et al., Tissue inhibitors of metalloproteinases: evolution, structure and function, Biochimica et Biophysica Acta 17(1477) (2000): 267-283.
Noma, T. et al., Beta-Arrestin-mediated beta 1-adrenergic receptor transactivation of the EGFR confers cardioprotection, The Journal of Clinical Investigation, 117 (2007): 2445-2458.
Dobaczewski, M. et al., The extracellular matrix as a modulator of the inflammatory and reparative response following myocardial infarction, Journal of Molecular and Cellular Cardiology 48 (2010): 504-511.
Frolova, E. G. et al., Thrombospondin-4 regulates fibrosis and remodeling of the myocardium in response to pressure overload, The FASEB Journal 26 (2012): 2363-2373.
Frangogiannis, N. G. et al., Critical Role of Endogenous Thrombospondin-1 in Preventing Expansion of Healing Myocardial Infarcts, Circulation 111 (2005): 2935-2942.
Frangogiannis, N. G., Matricellular proteins in cardiac adaptation and disease. Physiol Rev 92 (2012): 635-688.
Jaskelioff, M. et al., Telomerase reactivation reverses tissue degeneration in aged telomerase-deficient mice, Nature 469 (2011): 102-106.
Richardson, G. D. et al., Telomerase expression in the mammalian heart, The FASEB Journal 26 (2012): 4832-4840.
Lowes, B. D. et al., Myocardial gene expression in dilated cardiomyopathy treated with beta-blocking agents, N Engl J Med 346(18) (2002): 1357-1365.
Dobaczewski, M. et al., Transforming growth factor (TGF)-beta signaling in cardiac remodeling, Journal of Molecular and Cellular Cardiology 51 (2011): 600-606.
Jopling, C. et al., Zebrafish heart regeneration occurs by cardiomyocyte dedifferentiation and proliferation, Nature 25 (2010): 606-609.
Anversa, P. et al., Ventricular Myocytes Are Not Terminally Differentiated in the Adult Mammalian Heart, Circ Res 83, (1998): 1-14.
Beltrami, A. P. et al., Evidence that human cardiac myocytes divide after myocardial infarction, The New England Journal of Medicine 344 (2001): 1750-1757.
Glass, C. et al., Overexpression of TIMP-1 in Embryonic Stem Cells Attenuates Adverse Cardiac Remodeling Following Myocardial Infarction. Cell Transplantation 21 (2012): 1931-1944.
Matsushita, T. et al., Adeno-associated virus vectors can be efficiently produced without helper virus, Gene Therapy 5, (1998): 938-945.
Ayuso, E. et al., High AAV vector purity results in serotype- and tissue-independent enhancement of transduction efficiency, Gene Therapy 17 (2010): 503-510.
Blasco, M. A. et al., Differential regulation of telomerase activity and telomerase RNA during multi-stage tumorigenesis, Nat Genetics 12 (1996): 200-204.
Zincarelli, C. et al. Analysis of AAV Serotypes 1-9 Mediated Gene Expression and Tropism in Mice After Systemic Injection. Molecular Therapy 16 (2008): 1073-1080.
Korf-Klingebiel, M. et al., Conditional Transgenic Expression of Fibroblast Growth Factor 9 in the Adult Mouse Heart Reduces Heart Failure Mortality After Myocardial Infarction, Circulation 123 (2011): 504-514.
Mulero, F. et al., Imaging Cancer in Mice by PET, CT, and Combined PET-CT in Current Protocols in Mouse Biology (John Wiley & Sons) 1 (2011): 85-103.
Vera, E., The rate of increase of short telomeres predicts longevity in mammals. Cell Report 2 (2012): 732-737.
de Jesus, B. et al., Telomerase gene therapy in adult and old mice delays aging and increases longevity without increasing cancer, EMBO Molecular Medicine 4 (2012): 1-14.
Canela, A., Telomere Length Analysis, Methods Molecular Biology 371 (2007): 45-72.
Tomas-Loba, A. et al., A metabolic signature predicts biological age in mice, Aging Cell 12 (2013): 93-101.
Martinez, P. et al., RAP1 protects from obesity through its extratelomeric role regulating gene expression, Cell Report 3 (2013): 2059-2074.
Smyth, G. K. et al., Use of within-array replicate spots for assessing differential expression in microarray experiments. Bioinformatics 21, vol. 9 (2005): 2067-2075.
Subramanian, A. et al., Gene set enrichment analysis: a knowledge-based approach for interpreting genome-wide expression profiles, Proc Natl Acad Sci USA 102 (2005): 15545-15550.
Blasco, M., Telomere length, stem cells and aging. Nature Chemical Biology 3 (2007): 640-649.
Mcilrath, J. et al., Telomere Length Abnormalities in Mammalian Radiosensitive Cells, Cancer Research 61 (2001): 912-915.
Brouilette, S. W. et al., Telomere length, risk of coronary heart disease, and statin treatment in the West of Scotland Primary Prevention Study: a nested case-control study, Lancet 369 (2007): 107-114.
Moslehi, J. et al., Telomeres and mitochondria in the aging heart. Circulation Research 110 (2012): 1226-1237.

(56) References Cited

OTHER PUBLICATIONS

Blasco, M. A. et al., Telomere Shortening and Tumour Formation by Mouse Cells Lacking Telomerase RNA, Cell 91 (1) (1997): 25-34.
Gonzalez-Suarez, E. et al., Increased epidermal tumours and increased skin wound healing in transgenic mice overexpressing the catalytic subunit of telomerase, mTERT, in basal keratinocytes, The EMBO Journal 20, No. 11 (2001): 2619-30.
Merten, O-W. et al., Current issues in adeno-associated viral vector production, Gene Therapy 12 (2005): S51-61.
Buning, H., L. Perabo, et al., Recent developments in adeno-associated virus vector technology, The Journal of Gene Medicine 10 (2008): 717-733.
Niemeyer G.P. et al., Long-term correction of inhibitor-prone hemophilia B dogs treated with liver-directed AAV2-mediated factor IX gene therapy, Blood 113(4) (2009): 797-806.
Mas A. et al., Reversal of Type 1 Diabetes by Engineering a Glucose Sensor in Skeletal Muscle, Diabetes 55 (2006) 1546-1553.
Jiang, H., et al. Multiyear therapeutic benefit of AAV serotypes 2, 6, and 8 delivering factor VIII to hemophilia A mice and dogs. Blood. 108(1) (2006): 107-115.
Ghosh, A., et al. Efficient Whole-body Transduction with Trans-splicing Adeno-associated Viral Vectors. Mol Therapy 15(4) (2007): 750-755.
Tafuro S., et al. Inducible adeno-associated virus vectors promote functional angiogenesis in adult organisms via regulated vascular endothelial growth factor expression. Cardiovasc Res 83(4) (2009): 663-671.
Manno, C.S. et al. Successful transduction of liver in hemophilia by AAV-Factor IX and limitations imposed by the host immune response. Nature Med. 12(3) (2006): 342-347.
Stroes ES, et al. Intramuscular administration of AAV 1-lipoprotein lipase S447X lowers triglycerides in lipoprotein lipase-deficient patients. Arterioscler Thromb Vase Biol. 12 (2008): 2303-4.
Kaplitt, M. G. et al. Safety and tolerability of gene therapy with an adeno-associated virus (AAV) borne GAD gene for Parkinson's disease: an open label, phase I trial. The Lancet, 369 (9579) (2007): 2097-2105.
Maguire A.M., et al. Safety and efficacy of gene transfer for Leber's congenital amaurosis. N Engl J Med. 358(21) (2008): 2240-2248.
Bainbridge, J.W B., et al. Effect of Gene Therapy on Visual Function in Leber's Congenital Amaurosis. N Engl J Med. 358 (2008): 2231-2239.
Mingozzi, F. et al. CD8+ T-cell responses to adeno-associated virus capsid in humans. Nature Med. 13 (2007): 419-422.
Brantly, M. L., et al. Sustained transgene expression despite T lymphocyte responses in a clinical trial of rAAVI-AAT gene therapy. Proc Natl Acad Sci USA 106 (2009): 16363-16368.
Mingozzi F, et al. AAV-1-mediated gene transfer to skeletal muscle in humans results in dose-dependent activation of capsid-specific T cells. Blood. 114 (2009): 2077-2086.
Simonelli, F., et al. Therapy for Leber's Congenital Amaurosis is Safe and Effective Through 1.5 Years After Vector Administration. Mol Ther. 18(3) (2010): 643-650.
Inagaki, K., S. Fuess, et al. Robust systemic transduction with AAV9 vectors in mice: efficient global cardiac gene transfer superior to that of AAV8. Mol Ther 14(1) (2006): 45-53.
Foust, K.D. et al. Intravascular AAV9 preferentially targets neonatal neurons and adult astrocytes. Nature Biotechnology, 27 (2009): 59-65.
Duque S., et al. Intravenous administration of self-complementary AAV9 enables transgene delivery to adult motor neurons. Molecular Therapy 17(7) (2009): 1187-1196.
Samper E., et al. Restoration of telomerase activity rescues chromosomal instability and premature aging in Terc-/- mice with short telomeres. EMBO Rep. 2(9) (2001): 800-7.
Sebastian Brandt, TERT over-expression affects the growth of myocardial tissue derived from mouse embryonic stem cells, Differentiation 79 (2010): 1-8.
International Search Report and Written Opinion for PCT/EP2015/067875, dated Oct. 14, 2015.

* cited by examiner

Figure 1

| Heart infected with: | vector genomes/ diploid genome |
|---|---|
| AAV9-*Tert* (n=4) | 0,92 (+/- 0,03) |
| AAV9-eGFP (n=5) | 0,88 (+/- 0,04) |

TELOMERASE REVERSE TRANSCRIPTASE-BASED THERAPIES FOR TREATMENT OF CONDITIONS ASSOCIATED WITH MYOCARDIAL INFARCTION

This application is a National Stage application of PCT/EP2015/067875, filed 4 Aug. 2015, which claims priority to European Patent Application No. 14382311.0, filed 8 Aug. 2014, the contents of all of which are hereby incorporated by reference in their entireties.

FIELD OF INVENTION

This invention falls within the field of molecular biology, biotechnology and medicine. More particularly, it relates to compositions and methods useful for the treatment and prevention of conditions associated with myocardial infarction.

BACKGROUND OF THE INVENTION

Telomeres are specialized structures at the ends of chromosomes, which have a role in protecting the chromosome ends from DNA repair and degrading activities (10; 11). Mammalian telomeres consist of TTAGGG repeats bound by a multi-protein complex known as shelterin (11). A minimum length of TTAGGG repeats and the integrity of the shelterin complex are necessary for telomere protection (10; 11). Telomerase is a cellular reverse transcriptase (TERT, telomerase reverse transcriptase; also known as TP2; TRT; EST2; TCS1; hEST2) capable of compensating telomere attrition through de novo addition of TTAGGG repeats onto the chromosome ends by using an associated RA component as template (Terc, telomerase RNA component) (12). Telomerase is expressed in most adult stem cell compartments, however, this is not sufficient to maintain telomere length as evidenced by the fact that telomere shortening occurs with age in most human and mouse tissues (15; 61; 14).

Mice carrying homozygous deletion for the TERC gene (the telomerase RNA component) lack any detectable telomerase activity and showed progressive telomere shortening from one generation to the other at a rate comparable to the rate reported in human cells (65). Severe phenotypes typical of late generation TERC−/− mice (e.g. bone marrow aplasia and signs of premature aging) could be rescued by re-introducing a copy of the TERC gene (86). Multiple tissue degeneration arising in later generations in a conditional mouse model defective for TERT (the catalytic telomerase subunit) could be reversed upon telomerase reactivation even in aged mice (40).

In the context of wild-type mice, introducing an additional copy of the telomerase gene, which is expressed in a wide range of epithelial tissues, led to an increased wound healing capacity of the skin (66). When this allele was introduced in a tumour-resistant genetic background (Sp53/Sp16/SArf) remarkable delay of aging in concert with an increased median lifespan of 40% compared to mice not expressing the telomerase transgene was observed (24).

A virus (AAV) based telomerase gene therapy was found to be beneficial to extend health span, in the context of normal physiological aging in wild-type mice. In the study examining this benefit, adult and aged mice were subjected to AAV9-mTERT gene therapy to broadly express the catalytic subunit of mouse telomerase (mTERT). The health span of the TERT treated mice was significantly increased, and aging was decelerated, as indicated by a number of physiological parameters (glucose and insulin tolerance, osteoporosis, neuromuscular coordination, rota-rod, etc). In addition, their mean lifespan, compared to control groups, was increased by 24% and 13% in adult an old mice, respectively. A single intravenous administration of AAV9-TERT in adult mice resulted in an increase in telomere length in peripheral blood cells (26).

In the case of cardiovascular diseases (CVD), short telomeres have been linked to cardiac dysfunction both in mice and humans (63, 19, 20, 21, 64). In particular, mice with critically short telomeres owing to telomerase deficiency develop cardiomyopathy characterized impaired cell division, enhanced cardiomyocyte death and cellular hypertrophy, which are concomitant with ventricular dilation, thinning of the wall and cardiac dysfunction (19). Interestingly, analogous to the loss of the full regeneration capacity of the heart, expression of the telomerase essential genes Terc and Tert is lost within the first week of postnatal life (22, 23).

Heart failure is among the most common causes of mortality and morbidity worldwide, and its prevalence continues to increase. In spite of new therapies, cardiac remodeling and subsequent heart failure remain critical issues after myocardial infarction (1), highlighting the urgency of developing new therapeutic strategies.

SUMMARY

The invention provides compositions and methods useful for the treatment and prevention of conditions associated with myocardial infarction.

One aspect of the invention provides a method of treating a condition associated with myocardial infarction in a patient in need thereof comprising administering to the patient a nucleic acid vector comprising a coding sequence for telomerase reverse transcriptase (TERT). The condition associated with myocardial infarction is selected from the group consisting of a myocardial infarction, tissue damage resulting from myocardial infarction, fibrosis of the myocardium resulting from myocardial infarction, and reduced cardiac function resulting from myocardial infarction.

Another aspect of the invention provides a method of promoting myocardial tissue regeneration in a patient in need thereof comprising administering to the patient a nucleic acid vector comprising a coding sequence for telomerase reverse transcriptase (TERT).

Another aspect of the invention provides a method of reducing fibrosis of the myocardium in a patient in need thereof comprising administering to the patient a nucleic acid vector comprising a coding sequence for telomerase reverse transcriptase (TERT).

Another aspect of the invention provides a method of improving cardiac function in a patient in need thereof comprising administering to the patient a nucleic acid vector comprising a coding sequence for telomerase reverse transcriptase (TERT).

Another aspect of the invention provides a method of preventing myocardial infarction in a patient in need thereof comprising administering to the patient a nucleic acid vector comprising a coding sequence for telomerase reverse transcriptase (TERT).

Another aspect of the invention provides a method of promoting cardiomyocyte proliferation in a patient in need thereof comprising administering to the patient a nucleic acid vector comprising a coding sequence for telomerase reverse transcriptase (TERT).

In certain embodiments of these aspects, the patient treated has previously suffered a myocardial infarction.

In one embodiment, the TERT is encoded by a nucleic acid sequence comprising a sequence that is at least 90% identical to the sequence of SEQ ID NO: 1 or SEQ ID NO: 3. In one embodiment, the TERT is encoded by a nucleic acid sequence comprising the sequence of SEQ ID NO: 1 or SEQ ID NO: 3. In one embodiment, the TERT is encoded by a nucleic acid sequence consisting of the sequence of SEQ ID NO: 1 or SEQ ID NO: 3 In one embodiment, the TERT comprises an amino acid sequence that is at least 90% identical to the amino acid sequence of SEQ ID NO:2 or SEQ ID NO: 4. In one embodiment, the TERT comprises an amino acid sequence of SEQ ID NO:2 or SEQ ID NO: 4. In one embodiment, the TERT consists of the amino acid sequence of SEQ ID NO:2 or SEQ ID NO: 4. In one embodiment, the nucleic acid sequence encoding TERT is operably linked to a regulatory sequence that drives the expression of the coding sequence. In one embodiment, the vector is a non-integrative vector, such as an adeno-associated virus-based non-integrative vector. In one embodiment, the vector is an adeno-associated virus-based vector derived from a serotype 9 adeno-associated virus (AAV9). In one embodiment, the capsid of the adeno-associated virus-based vector is made of capsid proteins of the serotype 9 adeno-associated virus (AAV9), and the nucleic acid sequence contained in the capsid is flanked at both ends by internal terminal repeats corresponding to serotype 2 adenoassociated viruses. In one embodiment, the nucleic acid contained in the capsid comprises a fragment which encodes the amino acid sequence coding for TERT. In one embodiment, the vector comprises a regulatory sequence which is a constitutive promoter. In one embodiment, the regulatory sequence is the cytomegalovirus (CMV) promoter.

In one embodiment, the vector is administered directly to the cardiac tissue.

In yet further embodiments, the invention is directed to the following set of subject matters:

1. A method of treating a condition associated with myocardial infarction in a patient in need thereof comprising administering to the patient a nucleic acid vector comprising a coding sequence for telomerase reverse transcriptase (TERT).

2. The method of 1, wherein the condition associated with myocardial infarction is selected from the group consisting of a myocardial infarction, tissue damage resulting from myocardial infarction, fibrosis of the myocardium resulting from myocardial infarction, and reduced cardiac function resulting from myocardial infarction.

3. A method of promoting myocardial tissue regeneration in a patient in need thereof comprising administering to the patient a nucleic acid vector comprising a coding sequence for telomerase reverse transcriptase (TERT).

4. A method of reducing fibrosis of the myocardium in a patient in need thereof comprising administering to the patient a nucleic acid vector comprising a coding sequence for telomerase reverse transcriptase (TERT).

5. A method of improving cardiac function in a patient in need thereof comprising administering to the patient a nucleic acid vector comprising a coding sequence for telomerase reverse transcriptase (TERT).

6. A method of preventing myocardial infarction in a patient in need thereof comprising administering to the patient a nucleic acid vector comprising a coding sequence for telomerase reverse transcriptase (TERT).

7. A method of promoting cardiomyocyte proliferation in a patient in need thereof comprising administering to the patient a nucleic acid vector comprising a coding sequence for telomerase reverse transcriptase (TERT).

8. The method of any of 1-7, wherein the patient has previously suffered a myocardial infarction event.

9. The method of 8, wherein the vector is administered within twelve hours after the myocardial infarction event.

10. The method of 8, wherein the vector is administered within twenty-four hours after the myocardial infarction event.

11. The method of any of 1-10, wherein TERT is encoded by a nucleic acid sequence comprising a sequence that is at least 90% identical to the sequence of SEQ ID NO: 1 or SEQ ID NO: 3.

12. The method of any of 1-11, wherein TERT is encoded by a nucleic acid sequence comprising the sequence of SEQ ID NO: 1 or SEQ ID NO: 3.

13. The method of any of 1-12, wherein TERT is encoded by a nucleic acid sequence consisting of the sequence of SEQ ID NO: 1 or SEQ ID NO: 3

14. The method of any of 1-13, wherein TERT comprises an amino acid sequence that is at least 90% identical to the amino acid sequence of SEQ ID NO:2 or SEQ ID NO: 4.

15. The method of any of 1-14, wherein TERT comprises an amino acid sequence of SEQ ID NO:2 or SEQ ID NO: 4.

16. The method of any of 1-15, wherein TERT consists of the amino acid sequence of SEQ ID NO:2 or SEQ ID NO: 4.

17. The method of any of 1-16, wherein the nucleic acid sequence encoding TERT is operably linked to a regulatory sequence that drives the expression of the coding sequence.

18. The method of any of 1-17, wherein the vector is a non-integrative vector.

19. The method of any of 1-18, wherein the vector is an adeno-associated virus-based non-integrative vector.

20. The method of any of 1-19, wherein the vector is an adeno-associated virus-based vector derived from a serotype 9 adeno-associated virus (AAV9).

21. The method of 20, wherein the capsid of the adeno-associated virus-based vector is made of capsid proteins of the serotype 9 adeno-associated virus (AAV9), and the nucleic acid sequence contained in the capsid is flanked at both ends by internal terminal repeats corresponding to serotype 2 adenoassociated viruses.

22. The method of 21, wherein the nucleic acid contained in the capsid comprises a fragment which encodes the amino acid sequence coding for TERT.

23. The method of any of 1-22, wherein the vector comprises a regulatory sequence which is a constitutive promoter.

24. The method of 23, wherein the regulatory sequence is the cytomegalovirus (CMV) promoter.

25. The method of any of 1-24, wherein the vector is administered directly to the cardiac tissue.

26. A nucleic acid vector comprising a coding sequence for telomerase reverse transcriptase (TERT) for use in treating a condition associated with myocardial infarction.

27. The nucleic acid vector of 26, wherein the condition associated with myocardial infarction is selected from the group consisting of a myocardial infarction, tissue damage resulting from myocardial infarction, fibrosis of the myocardium resulting from myocardial infarction, and reduced cardiac function resulting from myocardial infarction.

28. A nucleic acid vector comprising a coding sequence for telomerase reverse transcriptase (TERT) for use in promoting myocardial tissue regeneration in a patient in need thereof.

29. A nucleic acid vector comprising a coding sequence for telomerase reverse transcriptase (TERT) for use in reducing fibrosis of the myocardium in a patient in need thereof.

30. A nucleic acid vector comprising a coding sequence for telomerase reverse transcriptase (TERT) for use in improving cardiac function in a patient in need thereof.

31. A nucleic acid vector comprising a coding sequence for telomerase reverse transcriptase (TERT) for use in preventing myocardial infarction in a patient in need thereof.

32. A nucleic acid vector comprising a coding sequence for telomerase reverse transcriptase (TERT) for use in promoting cardiomyocyte proliferation in a patient in need thereof.

33. The nucleic acid vector of any of 26-32, wherein the patient has previously suffered a myocardial infarction event.

34. The method of 33, wherein the vector is administered within twelve hours after the myocardial infarction event.

35. The method of 33, wherein the vector is administered within twenty-four hours after the myocardial infarction event.

36. The nucleic acid vector of any of 26-35, wherein TERT is encoded by a nucleic acid sequence comprising a sequence that is at least 90% identical to the sequence of SEQ ID NO: 1 or SEQ ID NO: 3.

37. The nucleic acid vector of any of 26-36, wherein TERT is encoded by a nucleic acid sequence comprising the sequence of SEQ ID NO: 1 or SEQ ID NO: 3.

38. The nucleic acid vector of any of 26-37, wherein TERT is encoded by a nucleic acid sequence consisting of the sequence of SEQ ID NO: 1 or SEQ ID NO: 3

39. The nucleic acid vector of any of 26-38, wherein TERT comprises an amino acid sequence that is at least 90% identical to the amino acid sequence of SEQ ID NO:2 or SEQ ID NO: 4.

40. The nucleic acid vector of any of 26-39, wherein TERT comprises an amino acid sequence of SEQ ID NO:2 or SEQ ID NO: 4.

41. The nucleic acid vector of any of 26-40, wherein TERT consists of the amino acid sequence of SEQ ID NO:2 or SEQ ID NO: 4.

42. The nucleic acid vector of any of 26-41, wherein the nucleic acid sequence encoding TERT is operably linked to a regulatory sequence that drives the expression of the coding sequence.

43. The nucleic acid vector of any of 26-42, wherein the vector is a non-integrative vector.

44. The nucleic acid vector of any of 26-43 wherein the vector is an adeno-associated virus-based non-integrative vector.

45. The nucleic acid vector of any of 26-44, wherein the vector is an adeno-associated virus-based vector derived from a serotype 9 adeno-associated virus (AAV9).

46. The nucleic acid vector of 45, wherein the capsid of the adeno-associated virus-based vector is made of capsid proteins of the serotype 9 adeno-associated virus (AAV9), and the nucleic acid sequence contained in the capsid is flanked at both ends by internal terminal repeats corresponding to serotype 2 adenoassociated viruses.

47. The nucleic acid vector of 46, wherein the nucleic acid contained in the capsid comprises a fragment which encodes the amino acid sequence coding for TERT.

48. The nucleic acid vector of any of 26-47, wherein the vector comprises a regulatory sequence which is a constitutive promoter.

49. The nucleic acid vector of 48, wherein the regulatory sequence is the cytomegalovirus (CMV) promoter.

50. The nucleic acid vector of any of 26-49, wherein the vector is administered directly to the cardiac tissue.

BRIEF DESCRIPTION OF THE FIGURES

FIG. 1: Ratio of viral genomes (AAV9-Tert and AAV9-eGFP) per diploid genome of analysed heart tissue sample. Deviation is shown in brackets.

DETAILED DESCRIPTION OF EMBODIMENTS OF THE INVENTION

Figure 2:
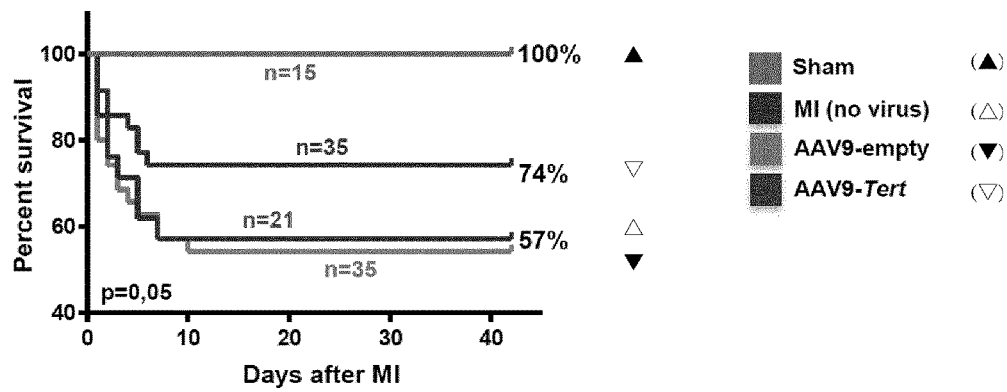
FIG. 2: Telomerase expression reduces lethal heart failure after MI and rescues cardiac function parameters. A) Kaplan-Meier survival curves after MI indicating 17% improved survival after Tert treatment and MI. Statistical analysis was calculated with log-rank test. No sham operated animal died. B-F) Echocardiography at 1 and 3 weeks in mice injected with AAV9-Tert, AAV9-empty or no virus (all MI); or sham mice (no virus, no MI) reveals functional improvement in the Tert group. B) LV end-systolic area, C) LV end-diastolic area, D) ejection fraction, E) longitudinal wall thickness, F) transversal wall thickness in the indicated number of mice was determined (E and F only at 1 week post MI).
Figure 2:
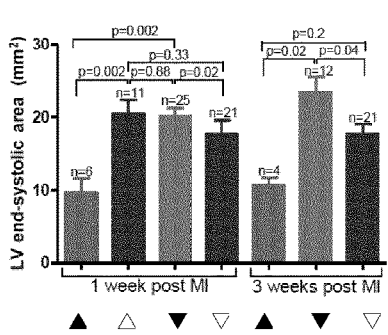
Figure 2:
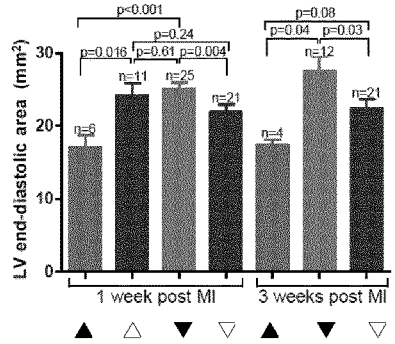
Figure 2:
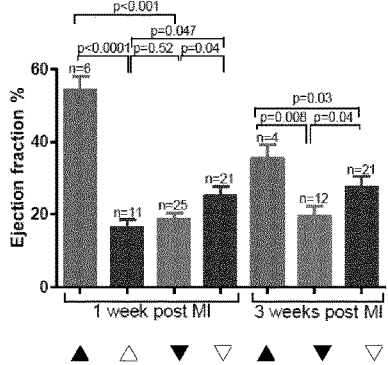
Figure 2:
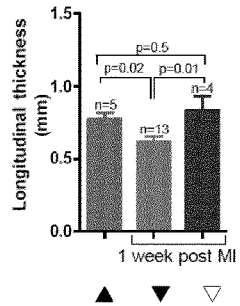
Figure 2:
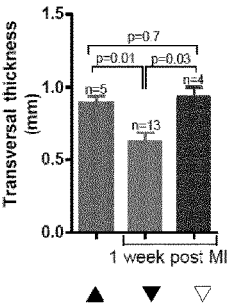

The invention provides compositions and methods useful for the treatment and prevention of conditions associated with myocardial infarction.

A "condition associated with myocardial infarction" includes myocardial infarction events, tissue damage resulting from myocardial infarction (including loss of cardiomyocytes), fibrosis of the myocardium resulting from myocardial infarction, reduced cardiac function resulting from myocardial infarction, As disclosed in the Examples, treatment of adult mouse heart with the telomerase gene therapy of the invention has beneficial effects following MI by aiding heart regeneration capacity, decreasing fibrosis, and significantly increasing survival time. Treatment with the telomerase gene therapy increase telomerase activation in the heart which improves cardiac functional and morphological parameters and significantly reduces heart failure mortality after MI. The treatment rescues gene expression changes associated to the failing heart, including changes in metabolism, and expression of fetal genes.

Accordingly, the invention provides methods of treating a patient suffering from a condition associated with myocardial infarction comprising administering to the patient an agent which increases the telomere length of the patient. In one embodiment, the agent prevents degradation of the chromosomal ends. In one embodiment, the agent increases the activity of telomerase reverse transcriptase (TERT). In one embodiment, the method of treatment is a gene therapy method comprises administering to the patient a nucleic acid vector comprising a coding sequence for telomerase reverse transcriptase (TERT).

In certain embodiments, the TERT sequence used in the gene therapy vector is derived from the same species as the subject. For example, gene therapy in humans would be carried out using the human TERT sequence. Gene therapy in mice would be carried out using the mouse TERT sequence, as described in the examples. In one embodiment, the TERT is encoded by the nucleic acid sequence as set forth in SEQ ID NO: 1 or SEQ ID NO: 3 (human TERT variants 1 and 2), or is an active fragment or functional equivalent of SEQ ID NO: 1 or SEQ ID NO: 3. The polypeptide sequence encoded by SEQ ID NO: 1 is set forth in SEQ ID NO: 2. The polypeptide encoded by SEQ ID NO: 3 is set forth in SEQ ID NO: 4. As used herein, "functional equivalent" refers to a nucleic acid molecule that encodes a polypeptide that has TERT activity or a polypeptide that has TERT activity. The functional equivalent may displays 50%, 60%, 70%, 80%, 90%, 95%, 98%, 99%, 100% or more activity compared to TERT encoded by SEQ ID NO: 1 or SEQ ID NO: 3. Functional equivalents may be artificial or naturally-occurring. For example, naturally-occurring variants of the TERT sequence in a population fall within the scope of functional equivalent. TERT sequences derived from other species also fall within the scope of the term "functional equivalent", in particular the murine TERT sequence given in SEQ ID NO: 5. In a particular embodiment, the functional equivalent is a nucleic acid with a nucleotide sequence having at least 75%, 80%>, 85%, 90%, 95%, 96%, 97%, 98%, 99%, 99.5%, 99.9% identity to SEQ ID NO: 1 or SEQ ID NO: 3. In a further embodiment, the functional equivalent is a polypeptide with an amino acid sequence having at least 75%, 80%, 85%, 90%, 95%, 96%, 97%, 98%, 99%, 99.5%, 99.9% identity to SEQ ID NO: 2 or SEQ ID NO: 4. In the case of functional equivalents, sequence identity should be calculated along the entire length of the nucleic acid. Functional equivalents may contain one or more, e.g. 2, 3, 4, 5, 10, 15, 20, 30 or more, nucleotide insertions, deletions and/or substitutions when compared to SEQ ID NO: 1 or SEQ ID NO: 3. The term "functional equivalent" also encompasses nucleic acid sequences that encode a TERT polypeptide with at least 75%, 80%, 85%, 90%, 95%, 96%, 97%, 98%, 99%, 99.5%, 99.9% sequence identity to the sequence as set forth in SEQ ID NO:2 or SEQ ID NO: 4, but that show little homology to the nucleic acid sequence given in SEQ ID NO: 1 or SEQ ID NO: 3 because of the degeneracy of the genetic code.

As used herein, the term "active fragment" refers to a nucleic acid molecule that encodes a polypeptide that has TERT activity or polypeptide that has TERT activity, but which is a fragment of the nucleic acid as set forth in SEQ ID NO: 1 or SEQ ID NO: 3 or the amino acid sequence as set forth in SEQ ID NO: 2 or SEQ ID NO: 4. An active fragment may be of any size provided that TERT activity is retained. A fragment will have at least 75%, 80%, 85%, 90%, 95%, 96%, 97%, 98%, 99%, 99.5%, 100% identity to SEQ ID NO: 1-4 along the length of the alignment between the shorter fragment and SEQ ID NO: 1-4.

Fusion proteins including these fragments can be comprised in the nucleic acid vectors needed to carry out the invention. For example, an additional 5, 10, 20, 30, 40, 50 or even 100 amino acid residues from the polypeptide sequence, or from a homologous sequence, may be included at either or both the C terminal and/or N terminus without prejudicing the ability of the polypeptide fragment to fold correctly and exhibit biological activity.

Sequence identity may be calculated by any one of the various methods in the art, including for example BLAST (Altschul S F, Gish W, Miller W, Myers E W, Lipman D J (1990). "Basic local alignment search tool". J Mol Biol 215 (3): 403-410) and FASTA (Lipman, D J; Pearson, W R (1985). "Rapid and sensitive protein similarity searches". Science 227 (4693): 1435-41; http://fasta.bioch. Virginia, edu/fasta_www2/fasta_list2. shtml) and variations on these alignment programs.

In one embodiment, the method of treatment is a gene therapy method and/or the nucleic acid vector used is a gene therapy vector. Gene therapy methods and vectors are well known in the art and generally comprise delivering a nucleic acid encoding a therapeutically active protein to a subject. The nucleic acid may be delivered in a number of ways including delivering naked DNA such as plasmid or mini-circles, the use of liposomes or cationic polymers or other engineered nano-particles containing the nucleic acid, or viral vectors that encapsidate the nucleic acid.

In a further embodiment, the gene therapy is achieved using stable transformation of organisms with an inducible expression system. Suitable inducible expression systems are known in the art and include the CRE-LOX recombinase based system which is suitable for use in mice and tetracycline-regulated which can be used in the treatment of human subjects.

In one embodiment the gene therapy vector is a viral vector. Viral gene therapy vectors are well known in the art. Vectors include integrative and non-integrative vectors such as those based on retroviruses, adenoviruses (AdV), adeno-associated viruses (AAV), lentiviruses, pox viruses, alphaviruses, and herpes viruses.

Using non-integrative viral vectors, such as AAV, seems to be particularly advantageous. In one aspect, this is because non-integrative vectors do not cause any permanent genetic modification. Second, the vectors target to adult tissues, avoiding having the subjects under the effect of constitutive telomerase expression from early stages of development. Additionally, non-integrative vectors effectively incorporate a safety mechanism to avoid over-proliferation of TERT expressing cells. Cells will lose the vector (and, as a consequence, the telomerase expression) if they start proliferating quickly.

Particular examples of suitable non-integrative vectors include those based on adenoviruses (AdV) in particular gutless adenoviruses, adeno-associated viruses (AAV), integrase deficient lentiviruses, pox viruses, alphaviruses, and herpes viruses. Preferably, the non-integrative vector used in the invention is an adeno-associated virus-based non-integrative vector, similar to natural adeno-associated virus particles. AAV preferentially targets post-mitotic tissues, which are considered more resistant to cancer than the highly proliferative ones. Examples of adeno-associated virus-based non integrative vectors include vectors based on any AAV serotype, i.e. AAV1, AAV2, AAV3, AAV4, AAV5, AAV6, AAV7, AAV8, AAV9, AAV10, AAV11 and pseudo-typed AAV. Tissue specificity is determined by the capsid serotype. Pseudotyping of AAV vectors and capsid engineering to alter their tropism range will likely be important to their use in therapy.

Vectors derived from adeno-associated viruses (AAVs) have emerged as one of the vectors of choice for many gene transfer applications because of their many desirable properties, including capability to transduce a broad range of tissues at high efficiency, poor immunogenicity and an excellent safety profile (67; 68), toxicity being absent in many preclinical models (69; 70; 71; 72; 73). AAV vectors transduce post-mitotic cells and can sustain long-term gene expression (up to several years) both in small and large animal models of disease (69; 70; 71; 72; 73). Safety and efficacy of AAV gene transfer has been extensively studied in humans with encouraging results in the liver, muscle, CNS, and retina (74, 75, 76; 77; 78).

AAV2 is the best characterized serotype for gene transfer studies both in humans and experimental models. AAV2 presents natural tropism towards skeletal muscles, neurons, vascular smooth muscle cells and hepatocytes. AAV2 is therefore a good choice of vector to target these tissues, in particular when using the methods or vectors of the invention to treat a condition associated with one of these tissues. For example, treatment of neuromuscular degeneration may be targeted to skeletal muscle and/or neurons in this way.

Newly isolated serotypes, such as AAV7, AAV8, and AAV9 have been successfully adopted in preclinical studies (28). Although limited immunologic responses have been detected in human subjects treated with AAV2 or AAV1 against the AAV capsid (74; 79; 80; 81), long term expression of the therapeutic gene is possible depending on the target tissue and the route of administration (80; 82). In addition, the use of non-human serotypes, like AAV8 and AAV9, might be useful to overcome these immunological responses in subjects, and clinical trials have just commenced (ClinicalTrials.gov Identifier: NCT00979238). Altogether, these encouraging data suggest that AAV vectors are useful tools to treat human diseases with a high safety and efficient profile.

The choice of adeno-associated viruses of wide tropism, such as those derived from serotype 9 adeno-associated virus (AAV9) is particularly advantageous when treating conditions associated with short telomere length. AAV9 viruses have shown efficient transduction in a broad range of tissues, with high tropism for liver, heart and skeletal muscle (83) and thus the beneficial effects of gene therapy can be achieved in more tissues. In addition, AAV9 vectors have the unique ability to cross the blood-brain-barrier and target the brain upon intravenous injection in adult mice and cats (84; 85).

One aspect of the invention provides a system in which the capsid (which is the part of the virus which determines the virus tropism) of the adeno-associated virus-based vector is made of capsid proteins of the serotype 9 adeno-associated virus (AAV9). In one embodiment of the viral vectors for use in the invention, the polynucleotide sequence packed in the capsid is flanked by internal terminal repeats (ITRs) of an adeno-associated virus, preferably of serotype 2 which has been extensively characterised in the art, and presents a coding sequence located between the ITRs. As set out above, the nucleic acid preferably codes for a functional TERT polypeptide. In one embodiment, the regulatory sequence operatively linked to the TERT coding sequence is the cytomegalovirus promoter (CMV), although other suitable regulatory sequences will be known to those of skill in the art.

When treating conditions associated with short telomere length, it is advantageous to target the treatment to the effected tissues. The choice of AAV serotype for the capsid protein of the gene therapy vector may be thus based on the desired site of gene therapy. If the target tissue is skeletal muscle, for example, in treating loss of neuromuscular coordination, AAV1- and AAV6-based viral vectors can be used. Both of these serotypes are more efficient at transfecting muscle than other AAV serotypes. AAV3 is useful for transfecting haematopoietic cells. A thorough review of AAV-based vectors for gene therapy can be found in Shi et al, (2008) "AAV-based targeting gene therapy" Am. J. Immunol. 4:51-65.

Alternatively, other viral vectors can be used in the present invention. Any vector compatible with use in gene therapy can be used in the present invention. Heilbronn & Weger (2010) Handb Exp Pharmacol. 197: 143-70 provides a review of viral vectors that are useful in gene therapy. In accordance with all the previous discussion, vectors comprising a coding sequence for telomerase reverse transcriptase (TERT) suitable for use in gene therapy are an important point for putting the invention into practice. Suitable gene therapy vectors include any kind of particle that comprises a polynucleotide fragment encoding the telomerase reverse transcriptase (TERT) protein, operably linked to a regulatory element such as a promoter, which allows the expression of a functional TERT protein demonstrating telomerase reverse transcriptase activity in the targeted cells. Preferably, TERT is encoded by the nucleic acid sequence as set forth in SEQ ID NO: 1 or SEQ ID NO: 3, or is an active fragment or functional equivalent of TERT.

The term gene therapy vector includes within its scope naked DNA molecules such as plasmids or mini-circles, i.e. circular DNA molecules which do not contain bacterial DNA sequences, provided that the TERT coding sequence and its linked regulatory element are inserted in the plasmid, as well as to more complicated systems, such as particles with the structure of virions (viral particles), comprising at least a capsid and at least a polynucleotide sequence, with a size that allows the polynucleotide sequence to be packed within the capsid in a manner similar to that of the native genome of the virus of origin of the capsid. The polynucleotide sequence must include a region where the TERT coding sequence and its linked regulatory element are inserted such that the telomerase reverse transcriptase protein can be expressed from that polynucleotide sequence once the viral particle has infected a cell.

In one embodiment, the gene therapy vector suitable for being used in the invention is a non-integrative vector, such as an adeno-associated virus-based non-integrative vector. For the purposes of the invention, the choice of non-integrative vectors seems to be particularly advantageous, because they do not cause any permanent genetic modification. Also, as stated before, such vectors incorporate a safety mechanism to avoid over-proliferation of TERT expressing cells that will lose the vector if the cells start proliferating quickly.

Adeno-associated virus-based vectors derived from a serotype 9 adeno-associated virus (AAV9) are preferred because the beneficial effects can be achieved in more tissues (see above). In one particularly preferred embodiment, the regulatory sequence operatively linked to the TERT coding sequence is the cytomegalovirus promoter (CMV). The nucleic acid sequence encoding TERT is operably linked to a regulatory sequence that drives the expression of the coding sequence. As used herein, the term "regulatory element" means a nucleic acid sequence that serves as a promoter, i.e., regulates expression of a nucleic acid sequence operably linked to the promoter. Such "regulatory elements" or "promoters" can control the expression of linked nucleic acid sequences either constitutively or inducible.

The regulatory sequence may be a constitutive promoter. An example of a regulatory sequence which is a constitutive promoter is the cytomegalovirus (CMV) promoter.

The expression of TERT following gene therapy according to the invention persists for a time of several months to several years. In mice, TERT expression was detectable after 5 months. In monkey, gene expression following gene therapy with an AAV-based vector has been detected up to 6 years after treatment and up to 8 years in dogs (Rivera et al Blood 2005, and 69). Frequent repetition of treatment using the methods and vectors of the invention is therefore not necessary. In one embodiment of the invention, the subject is treated once. In an alternative embodiment, the subject is treated initially, and is then treated again once TERT expression levels decrease by about 50% of those attained immediately following treatment. Treatment may be repeated with the same or alternative vector to maintain the reduction in age-related disorders if necessary, for example annually, or once every 5 years or once a decade. When administering a second or subsequent dose, it may be necessary to use a different gene therapy vector, for example when using an AAV-based vector the second and subsequent administrations may be a vector with a capsid derived from a different serotype than that used for the first administration. It is possible that a subject may develop neutralising antibodies to the first gene therapy vector, making it ineffective if administered a second or subsequent time (Amado et al (2010) Science Translational Medicine 2(21):21ra16).

In particular embodiments, the gene therapy treatment is administered to a patient after that patient has suffered a myocardial infarction. It is preferable to administer the treatment as soon as possible after the myocardial infarction, for example within twelve hours, twenty-four hours, thirty-six hours, forty-eight hours, sixty hours, seventy-two hours, or eighty-four hours after the myocardial infarction event.

In the treatment of a condition associated with myocardial infarction, it is preferable to use the AAV9 vector. While this vector has a wide tropism, it preferentially transduces cardiac tissue, thereby allowing use of a low dose of the vector resulting in minimal transduction of non-cardiac tissue.

In one embodiment the vector is administered directly into the cardiac tissue, further reducing the potential of cross-reactivity of other tissues. Direct administration to the cardiac tissue is also advantageous as it allows for a lower dose of vector to be effective in the treatment. In one embodiment, the vector is administered directly to the cardiac tissue in a dose which is effective to transduce cardiac tissue with minimal transduction to liver, brain, or other non-cardiac tissue.

As demonstrated in the Examples, treatment of adult mouse heart with the gene therapy of the invention improves cardiac functional and morphological parameters and significantly reduces heart failure mortality after a myocardial infarction event. Specific beneficial effects of the gene therapy treatment following MI included promotion of cardiac tissue regeneration capacity, decreased fibrosis, and significantly increased survival time of the treated mice.

Importantly, the treatment rescued gene expression changes associated with a failing heart, including changes in metabolism, and expression of fetal genes. Moreover, sustained TGFβ-signaling and matrix remodeling was found in the treated heart as was induction of cardio-protective pathways such as the EGF pathway. Gene expression changes induced by the treatment are enriched in the regenerative gene expression signature described in neonatal mice, which have a full regenerative potential.

Accordingly, the methods of treatment of the invention have the effect of treating and/or preventing conditions associated with myocardial infarction. In a further aspect, therefore, the invention refers to a gene therapy method or the use of a nucleic acid vector as described above, for use in the treatment or prevention in a patient of a condition associated with myocardial infarction, including but not limited to myocardial infarction events, tissue damage resulting from myocardial infarction (including loss of cardiomyocytes), fibrosis of the myocardium resulting from myocardial infarction, reduced cardiac function resulting from myocardial infarction.

In one embodiment, the gene therapy method results in an increase lifespan of the treated patient, based on the prevention or delay of a myocardial infarction. In one embodiment, the gene therapy prevents or reduces fibrosis of the cardiac tissue. In one embodiment, the gene therapy improves cardiac function. In one embodiment, the gene therapy promotes cardiac tissue regeneration. In one embodiment, the gene therapy promotes cardiomyocyte proliferation. In particular embodiments, the patient administered the gene therapy has suffered a previous myocardial infarction event.

The effectiveness of treatment of the conditions associated with myocardial infarction can be measured by various methods known in the art. In one embodiment, the effectiveness of the treatment is measured by an increase in lifespan of a treated patient suffering from a condition associated with myocardial infarction as compared to the expected lifespan of an untreated patient suffering from the same condition. In certain embodiments, the lifespan is extended by 5%, 10%, 15%, 20%, 30%, 40%, 50%, or more, with reference to the expected lifespan for a patient suffering from the same condition.

The gene therapy treatment is useful in preventing or delaying the occurrence of a myocardial event in a patient who has already suffered a previous myocardial event. In this embodiment, the effectiveness of the treatment can be measured by a delayed onset of a subsequent myocardial infarction after a prior myocardial infarction. In certain embodiments, the delay in the onset of a subsequent myocardial infarction of a treated patient is extended by 5%, 10%, 15%, 20%, 30%, 40%, 50%, or more, with reference to the expected timing of subsequent myocardial infarction for an untreated patient.

In one embodiment, the effectiveness of the treatment is measured by a reduction in fibrosis of the myocardium resulting from myocardial infarction. In certain embodiments, the reduction in fibrosis of the myocardium resulting from myocardial infarction is reduced by 5%, 10%, 15%, 20%, 30%, 40%, 50%, or more, with reference to the fibrosis in the myocardium prior to the treatment. Fibrosis can be measured using various techniques known in the art. In one embodiment, fibrosis is measured by a pathological analysis, such as determination of fibrotic areas (scar) using Masson's trichrome staining.

In one embodiment, the effectiveness of the treatment is measured by an increase in cardiac function following myocardial infarction. In certain embodiments, the cardiac function following myocardial infarction is increased by 5%, 10%, 15%, 20%, 30%, 40%, 50%, or more, with reference to the level of cardiac function prior to treatment. Cardiac function can be measured using various techniques known in the art. In one embodiment, cardiac function is measure using echocardiography. In one embodiment, cardiac function is measured using Micro-PET Imaging. In another embodiment, cardiac function is measured based on kidney function, wherein a reduction in kidney function in a patient indicates a reduction in cardiac function in the patient. In another embodiment, cardiac function is measured based on the urea level in urine, wherein a reduction in urea level in the urine of a patient indicates a reduction in cardiac function in the patient.

The efficacy of the treatment can also be measured by directly determining telomere length in sample taken from the patient. Telomere length can be measured, for example, by using standard hybridization techniques, such as fluorescence in situ hybridization (FISH), Quantitative Fluorescent in situ hybridization (Q-FISH), or High Throughput Quantitative Fluorescent in situ hybridization (HT Q-FISH). (66). Telomere length can also be measured as described in Canela et al. (56).

In a particular embodiment, samples are taken from the patient undergoing treatment throughout the course of the treatment so that both absolute telomere length and the rate of telomere lengthening or shortening over the course of treatment can be determined. Samples may be taken every day during the course of treatment, or at longer intervals. In one embodiment, samples are taken once a week, once every two week, once every three weeks, once every 4 weeks, once every five weeks, once every six weeks or longer.

Comparison of telomere length can be measured by comparing the proportion of short telomeres in a sample taken from a patient. In one embodiment, the proportion of short telomeres is the fraction of telomeres presenting an intensity below the mean intensity of the sample as measured by a in situ hybridization technique, such as FISH or Q-FISH. In embodiment, the proportion of short telomeres is the fraction of telomeres presenting an intensity 75%, 70%, 65%, 60%, 55%, 50%, 45%, 40% or more below the mean intensity of the sample. In one particular embodiment, the proportion of short telomeres is the fraction of telomeres presenting an intensity 50% or more below the mean intensity of the sample.

In another embodiments, the proportion of short telomeres is the fraction of telomeres below a certain length, e.g. 8 kb, 7 kb, 6 kb, 5 kb, or shorter In one embodiment, the proportion of short telomeres is the fraction of telomeres 8 kb or shorter. In another embodiment, the proportion of short telomeres is the fraction of telomeres 7 kb or shorter. In another embodiment, the proportion of short telomeres is the fraction of telomeres 6 kb or shorter. In another embodiment, the proportion of short telomeres is the fraction of telomeres 5 kb or shorter. In another embodiment, the proportion of short telomeres is the fraction of telomeres 4 kb or shorter. In another embodiment, the proportion of short telomeres is the fraction of telomeres 3 kb or shorter.

In one embodiment, the effectiveness of the treatment is measured by a decrease in the proportion of short telomeres in sample taken from a treated patient suffering from a condition associated with myocardial infarction as compared to a control sample. In one embodiment, the proportion of short telomeres in a sample taken from a treated patient is decreased by 10%, 20%, 30%, 40%, 50%, 60%, 70%, or greater as compared to a control sample. In one embodiment, the control sample is a sample taken from the same patient prior to the treatment, or taken at an earlier stage of the treatment. In another embodiment, the control sample is a sample taken from a patient suffering from the same condition and not provided the treatment.

In a further aspect, the invention is applied to the subject by administering a pharmaceutical composition comprising an effective amount of any one of the gene therapy vectors compatible with the invention described above.

A "pharmaceutical composition" is intended to include the combination of an active agent with a carrier, inert or active, making the composition suitable for diagnostic or therapeutic use in vitro, in vivo or ex vivo.

"Composition" is intended to mean a combination of active agent and another compound or composition, inert (for example, a detectable agent or label) or active. An "effective amount" is an amount sufficient to effect beneficial or desired results. An effective amount can be administered in one or more administrations, applications or dosages.

They will usually include components in addition to the active component (such as the gene therapy vector) e.g. they typically include one or more pharmaceutical carrier(s) and/or excipient(s). A thorough discussion of such components is available in Gennaro (2000) Remington: The Science and Practice of Pharmacy. 20th edition, ISBN: 0683306472.

Compositions will generally be administered to a subject in aqueous form. Prior to administration, however, the composition may have been in a non-aqueous form. For instance, although some viral vectors are manufactured in aqueous form, then filled and distributed and administered also in aqueous form, other viral vectors are lyophilised during manufacture and are reconstituted into an aqueous form at the time of use. Thus a composition of the invention may be dried, such as a lyophilised formulation. The composition may include preservatives such as thiomersal or 2-phenoxyethanol. It is preferred, however, that the composition should be substantially free from (i.e. less than 5 µg/nif) mercurial material e.g. thiomersal-free.

To control tonicity, it is preferred to include a physiological salt, such as a sodium salt. Sodium chloride (NaCl) is preferred, which may be present at between 1 and 20 mg/ml e.g. about 10+2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The composition may include material for a single administration, or may include material for multiple administrations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Compositions of the invention for use in humans are typically administered in a dosage volume of about 0.5 ml, although a half dose (i.e. about 0.25 ml) may be administered to children.

As well as methods of treatment described herein, the invention also provides a nucleic acid sequence encoding a TERT for use in therapy. The invention also provides a nucleic acid vector comprising a coding sequence for telomerase reverse transcriptase (TERT), for use in a method of therapy and a gene therapy vector comprising a coding sequence for telomerase reverse transcriptase (TERT), for use in a method of therapy. In particular, the therapy may be treating or preventing a condition associated with myocardial infarction. As described for methods of treatment, the TERT nucleic acid sequence may be the sequence as recited in SEQ ID NO: 1 or SEQ ID NO: 3 or a fragment or functional equivalent thereof. The TERT protein may have a sequence as recited in SEQ ID NO: 2 or SEQ ID NO: 4, or a fragment or functional equivalent thereof.

The term "patient" refers to a mammal. In certain embodiments the patient is a rodent, primate, ungulate, cat, dog, or other domestic pet or domesticated mammal. In certain embodiments, the mammal is a mouse, rat, rabbit, pig, horse, sheep, cow, domestic cat or dog, or a human. In a preferred embodiment, the patient is a human.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

EXAMPLES

Example 1—Mouse Model of Myocardial Infarction

A clinical mouse model of myocardial infarction (MI) after coronary artery ligation, which resembles the situation found in the human heart after acute heart failure was developed. The adeno-associated viruses of serotype 9-MV9, which preferentially transduces the heart (28, 83, 55) was used as the gene therapy vector to deliver wild-type TERT expression specifically to the heart.

Mice

Male mice of a FVB/N background were produced and housed at the specific pathogen-free barrier area of the CNIO, Madrid. All animal procedures were approved by the CNIO-ISCIII Ethics Committee for Research and Animal Welfare (CEIyBA) and conducted in accordance to the recommendations of the Federation of European Laboratory Animal Science Associations (FELASA).

Viral Production Measurement of Virus Transduction Efficiency

Viral vectors were generated as described by Matsushita (48), and purified as previously described (49). The titres of viral genomes particles were determined by quantitative real time PCR. To assess viral tropism a control group of mice was injected with different concentrations of a virus carrying eGFP or Tert under the control of CMV promoter following the methodology described before. At 4 weeks post-injection mice were sacrificed and subjected to either pathological analysis or eGFP and Tert expression assessments. Quantification of eGFP immunostainings was determined by counting the number of peroxidase stained cells over the total number of hematoxylin-stained cells (liver and brain), or the peroxidase stained area relative to total section area (heart). Telomerase expression in different tissues was analysed by western blot analysis, quantitative RT-PCR and TRAP (telomerase repeat amplification protocol) assay following the previously described protocol (50). Viral genome copy number was assessed as previously detailed (51) with specific AAV9 primers, from heart DNA samples 4 weeks post injection.

Myocardial Infarction

After weaning, five mice were housed per cage and fed ad libitum of a non-purified diet (n° 2018, Harlan). MI was induced in male mice by permanent left anterior descending coronary artery (LAD) ligation under isofluorane anaesthesia. The analgesic bupenorphine was administered via intraperitoneal injections before the procedure. A sham operation was performed in control and injected mice. Sham operation consists of the same surgery procedure except from ligation of the LAD. The date of euthanasia was used to estimate mouse survival. For an assessment of post MI survival, mice were followed and inspected daily up to 6 weeks after LAD-ligation.

Echocardiography and Micro-PET

Transthoracic echocardiography was performed with a high-resolution Vevo770 in mice that were sedated with 1 to 2% isoflurane and placed on a heating pad as described (52). Micro-PET Imaging was performed as previously described (53).

Histology

Hearts were fixed in phosphate-buffered 4% formaldehyde and embedded in paraffin and sectioned (2 mm in thickness) from basal, midventricular, and apical regions using a heart slicer (Zivic instruments, HSMS001-1). Hearts slide sections (5 mm) were stained with Masson's trichrome. Infarct size and fibrotic length were calculated as the average ratio of scar length to total LV circumference of midventricular sections. Interstitial fibrotic area was performed on Masson's trichrome stained transverse heart sections in a semi-quantative way using the ImageJ software. Three images per heart from non-infarcted area were analyzed.

Immunohistochemistry and immunofluorescence was performed on deparaffinised tissues and processed with the indicated antibodies: Anti-eGFP (Abcam, ab290); anti-Vimentin (D21H3; Cell Signaling, 5741); anti-heavy chain cardiac Myosin (Abcam, ab15); anti-Troponin T (Thermo Scientific, Ab-1); anti-KI67 (Abcam, ab16667); anti-active caspase 3 (Abcam, ab13847).

Quantitative Real-Time PCR and Western Blots

Total RNA from tissues was extracted with with Qiagen's RNeasy mini kit according to the manufacturer's instructions. Before processing, RNA samples were DNase I treated. Quantitative real-time PCR was performed using an ABI PRISM 7700 (Applied Biosystems), using the following primers:

```
Actin- FW:
                                        (SEQ ID NO: 7)
GGCACCACACCTTCTACAATG;

Actin-RV:
                                        (SEQ ID NO: 8)
GTGGTGGTGAAGCTGTAG;

TERT-FW:
                                        (SEQ ID NO: 9)
GGATTGCCACTGGCTCCG;

TERT-RV:
                                        (SEQ ID NO: 10)
TGCCTGACCTCCTCTTGTGAC;

ANP-FW:
                                        (SEQ ID NO: 11)
GTGGCTTGTGGGAAAATAGTTGA;

ANP-RV:
                                        (SEQ ID NO: 12)
CTGGCTTGATGATCTGCCTTTAC;

β-MHC-FW:
                                        (SEQ ID NO: 13)
CCAATGAGTACCGCGTGAA;
```

```
β-MHC-RV:
                                      (SEQ ID NO: 14)
ACAGTCATGCCGGGATGAT;

BMPRB1-FW:
                                      (SEQ ID NO: 15)
CCCTCGGCCCAAGATCCTA;

BMPRB1-RV:
                                      (SEQ ID NO: 16)
CCACAGGCATTCCAGAGTCATC;

FGFR3-FW:
                                      (SEQ ID NO: 17)
GGAGGACGTGGCTGAAGAC;

FGFR3-RV:
                                      (SEQ ID NO: 18)
GGAGCTTGATGCCCCCAAT;

IRF7-FW:
                                      (SEQ ID NO: 19)
GAGACTGGCTATTGGGGGAG;

IRF7-RV:
                                      (SEQ ID NO: 20)
GACCGAAATGCTTCCAGGG;

ITGB6-FW:
                                      (SEQ ID NO: 21)
CAACTATCGGCCAACTCATTGA;

ITGB6-RF:
                                      (SEQ ID NO: 22)
GCAGTTCTTCATAAGCGGAGAT.
```

Statistical analyses (student's t-test) were performed on delta-delta Ct values. Western blots were made with whole cell extracts from the indicated tissues with the following antibodies: Anti-h/TERT 1 (Calbiochem), anti-GAPDH (Sigma). Quantification was done using the Scion Image Software.

Telomere Analysis

Q-FISH determination on paraffin-embedded tissue sections and HT-qFISH (in peripheral blood) was done as previously described (54, 55, 56). High throughput Q-FISH (HT-QFISH) TL analysis on blood samples HT-QFISH was performed as described (56). Briefly, peripheral blood was extracted from the facial vein before euthanizing animals, red blood cells lysed, leukocytes plated, fixed and subjected to Tel-Q-FISH. Fluorescence intensities were converted into Kb using L5178-R and L5178-S cells as calibration standards, which have stable TLs of 79.7 kb and 10.2 kb, respectively (62). Samples were analysed in duplicate, or triplicate in the case of calibration standards in the unbiased automated OPERA imaging system.

Serum Metabolite Analysis

Blood samples were collected in tubes without any anticoagulant, 6 weeks after MI. Samples were maintained on ice for 20 minutes and the serum supernatant was frozen and kept at 80° C. until they were analyzed to minimize freeze-thaw degradation (57). Serum urea concentration in mice (groups and numbers of mice depicted) was determined in an ABX Pentra400 serum analyzer (Horiba Medical). Additionally, high-throughput analysis of serum levels was measured with RodentMap v3.0 (Myriad RBM).

Gene Expression Analysis

Total RNA from frozen heart samples was extracted with Qiagen RNeasy kit, RNA integrity analysed in a Agilent Bioanalyzer (samples with RNA integrity index <7.8 were discarded) and analysed on Agilent's Mouse Genome DNA microarray following the manufacturer instructions and (58). Briefly, differentially expressed genes were obtained by applying linear models using the R limma package (59) (Bioconductor project, http://www.bioconductor.org).

To account for testing of multiple hypotheses, the estimated significance level (p value) was adjusted using the Benjamini & Hochberg False Discovery Rate (FOR) correction. Those genes with FOR <0.15 were selected as differentially expressed between Tert, empty virus injected hearts and sham operated controls.

Gene set enrichment analysis (GSEA) was applied using annotations from Reactome and KEGG. Genes were ranked based on limma moderated t statistic. After Kolmogorov-Smirnoff testing, those gene sets showing FOR <0.1 (60) were considered enriched between classes under comparison.

Statistical Analysis

A Log Rank test was used to calculate the statistical differences in the survival curves of the different mice cohorts. An unpaired t-student test was used to calculate statistical significance of mRNA and protein expression levels, TRAP, heart functional parameters, scar size and interstitial fibrosis. Mann-Whitney-U test was used for serum parameters. Pathological assessment either through heart observation after Masson's trichrome staining or FDG-PET scans were calculated with the x2 test.

Example 2—Downregulation of Mouse Tert Expression in the Heart During the First Week after Birth We first set out to determine whether mouse Tert expression is downregulated in heart during the first week of life, similarly to that previously described for mouse telomerase RNA component in different mouse tissues (22), Terc, as well as for Tert expression in the rat (23). To this end, we isolated neonatal hearts at days 1, 3, 7 and 10 and determined mouse Tert expression by qRT-PCR. We observed a significant dowregulation of mouse Tert mRNA levels from day 7 after birth.

Example 3—Targeting AAV9-Tert Specifically to the Heart

AAV9 is known to preferentially target the heart and the liver when administered systemically, although the efficiency of targeting hepatocytes is around 10-fold lower than that of targeting cardiomyocytes (29). We used this differential transduction efficiency to find a minimal dose of AAV9 vectors that would specifically target the heart, with minimal transduction of the liver, and other tissues. Under our experimental conditions, a dose $5 \times 10^{11}$ ug/mouse of a AAV9 reporter vector (AAV9-CMV-eGFP) could transduce more than 60% of heart cells, as shown by eGFP immunohistochemistry (IHC), but less than 1.2% of liver and brain cells. To estimate the transduction efficiency of the telomerase vector 22 (AAV9-CMV-Tert; hereafter AAV9-Tert), we compared the viral genome copy number per diploid genome in hearts transduced with either the eGFP reporter vector or the AAV9-Tert vector (FIG. 1). We found similar numbers of viral genome copies per cell, indicating similar transduction efficiency for AAV9-eGFP and AAV9-Tert in the heart. Using co-immunostaining with eGFP and markers of either cardiomyocytes (beta-myosin heavy chain, β-MHC) or fibroblasts (vimentin), we found that within the myocardium, AAV9 preferentially targets cardiomyocytes (>60% eGFP positive cardiomyocytes) while we found no evidence for infection of fibroblasts. Specific targeting of Tert to the heart was also confirmed by qRT-PCR showing a ~400 fold induction of Tert mRNA amounts in the heart of treated mice compared to non-treated mice, while Tert mRNA upregulation was 40-fold lower in the liver of treated mice. Tert mRNA expression levels in heart remained high during at least 2 months as indicated by >200 fold increased expression in AAV9-Tert treated mice compared to those treated with the empty vector. Finally, increased Tert mRNA expression was paralleled by increased TERT protein expression and increased telomerase activity in the AAV9-Tert treated hearts compared to non-treated mice and AAV9-empty treated controls. Together, these results indicate that we achieved specific Tert expression in the adult heart.

Example 4—Telomerase Targeting to the Heart does not Alter Heart Morphology

Constitutive Tert transgenic expression in the heart from embryonic development onwards results in heart hypertrophy (25). Thus, we first set to determine whether AAV9-Tert treatment during adulthood had any undesired effects on heart morphology. AAV9-Tert treatment in the absence of myocardial infarction (MI) did not change the normal heart structure nor did produce any signs of cardiac hypertrophy as assessed 9-10 weeks after virus administration. Further supporting a normal structure of the heart, we found normal expression of beta-myosin heavy chain (β-MHC) in AAV9-Tert treated hearts. These results indicate that Tert over-expression by means of AAV9 gene therapy does not have any of the adverse effects previously reported for constitutive Tert transgenic expression in the heart.

Example 5—Telomerase Gene Therapy Reduces Mortality after MI

To assess the therapeutic potential of telomerase activation during adulthood in prevention of heart failure after MI, we used a bona fide mouse pre-clinical model of myocardial infarction after coronary artery ligation, previously shown to recapitulate heart failure induced by MI30. Cardiac specific AAV9-10 mediated transgene expression reaches its maximum after around 2 weeks and remains stable thereafter (31). Even though expression emerges already very shortly after intravenous injection we decided to induce MI 2-3 weeks after virus administration to assure Tert levels are maximal. Furthermore, since we were interested in regeneration and remodelling processes after acute infarction, which in humans predominantly occurs in the adult life, we used adult (1-year old) mice. All mice under experimentation were males to avoid gender bias.

Interestingly, a single treatment with AAV9-Tert three weeks prior to artery ligation, was sufficient to rescue mouse survival post infarction, with more than 74% of the AAV9-Tert treated mice surviving infarct compared to only 57% of those treated with the empty vector (FIG. 2A). Thus, telomerase activation in adult mice significantly reduces mortality by heart failure after MI in a bona fide mouse model for the human condition.

Example 6—Telomerase Gene Therapy Improves Cardiac Function after MI

To investigate how telomerase expression results in lower mortality rates upon MI, cardiac function was assessed by 2-dimensional echocardiography at 1 and 3 weeks after LAD ligation. Cardiac dimensions such as left ventricle systolic and diastolic area were strongly increased after MI compared to the sham operated (no MI) mice (FIG. 2B,C), which was also accompanied by decreased cardiac ejection fraction (FIG. 2D). Importantly, both the cardiac dimensions and the ejection fraction were significantly rescued in mice that received the Tert gene therapy but not in those that received the empty vector (FIG. 2B-D).

The rescue in cardiac function parameters upon Tert treatment was also evidenced by a similar longitudinal and transversal heart wall thickness in both the Tert treated and the sham operated mice as compared to a marked decrease in these parameters in mice treated with the AAV9-empy vector (FIG. 2E,F).

Figure 3:
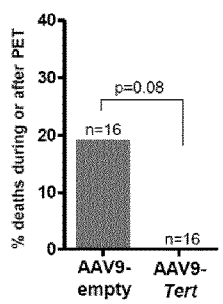
FIG. 3: FDG-PET scan reveals reduced infarct severity in AAV9-Tert treated mice and coincides with smaller fibrotic scar sizes and less interstitial fibrosis after MI. A) Percentage of AAV9-empty or AAV9-Tert mice that died during or shortly after PET scan. B) Infarct severity in AAV9-Tert and AAV9-empty cohorts was assessed in in vivo FDG-PET scans. A higher number of hearts with signal loss was found in the AAV9-empty group. C) Representative PET scan images of a fully functional heart (left) and failing hearts after MI (right). D) Average scar length relative to the LV endocardial circumference of indicated groups. E) Interstitial fibrotic area relative to total area measured in the infarct remote myocardium. Number of animals and statistical analysis (student's t-test) are depicted.
Figure 3:
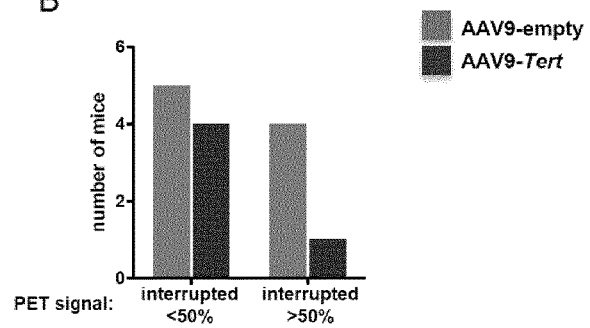
Figure 3:
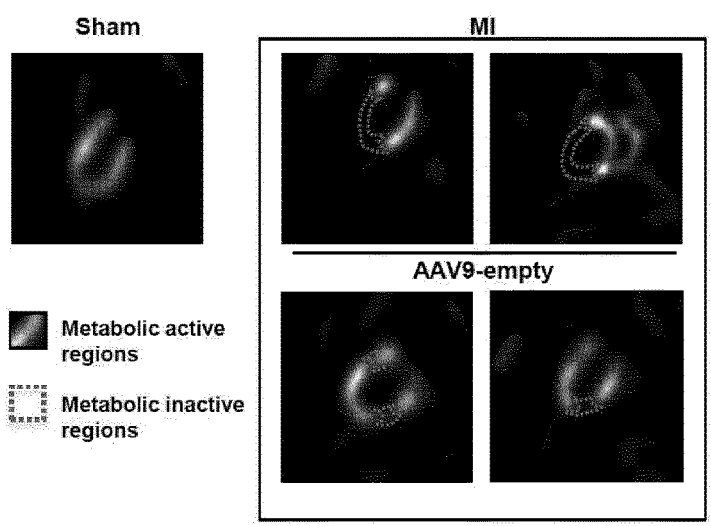
Figure 3:
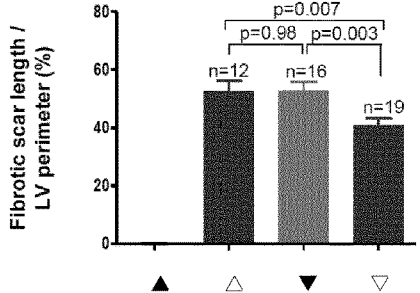
Figure 3:
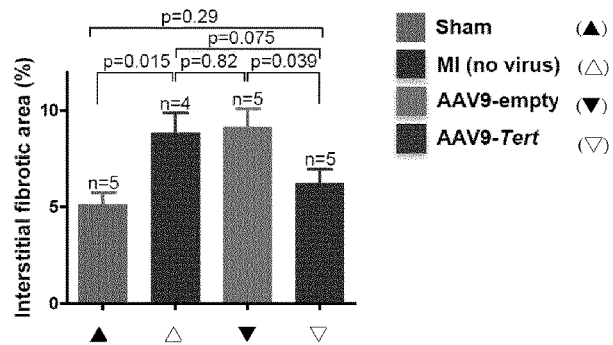

Next, we performed FDG-PET scan analysis, a diagnostic tool commonly used to assess infarct severity in vivo, as it measures metabolic activity in the heart via determining glucose uptake by cardiomyocytes. In particular, heart infarct results in decreased metabolic activity at the damaged regions (32). First, we noticed that AAV9-Tert treated mice present a better survival to the PET procedure per se, which involves anaesthesia and may result in death of mice subjected to MI (FIG. 3A). Of note, survival curves shown in FIG. 2A do not include mice used for PET. As expected, all mice showed reduced PET signals indicative of MI, however, we observed less severe infarcts (characterised by >50% loss of the PET signal) in the AAV9-Tert treated group compared to the AAV9-empty treated group (FIG. 3B-C). These results indicate that AAV9-Tert treated hearts show a better preservation of metabolically active regions compared to the AAV9-empty group upon MI.

Six weeks after MI, we performed full pathological analysis including determination of heart scar length using Masson's trichrome staining. We found that AAV9-Tert treated mice presented smaller infarcts compared to AAV-empty or no virus controls, as determined by the ratio of scar length to endocardial circumference (FIG. 3D). In addition, AAV9-Tert mice developed less interstitial fibrosis in the non-infarcted region of the left ventricle compared to the AAV9-empty group (FIG. 3E). Together, these findings indicate that a single AAV9-Tert treatment resulted in increased survival of the myocardium and smaller infarct sizes, thus preventing heart functional decline after MI.

Example 7—Telomerase Treatment Rescues Short Telomeres in the Heart Cardiomyocytes Critical telomere shortening causes heart dysfunction in mice. In particular, telomerase deficient mice bearing critically short telomeres present heart phenotypes resembling those of heart dysfunction in humans, including heart hypertrophy (19). As telomerase main function is to elongate critically short telomeres, here we set out to address the effects of Tert treatment on heart telomere length (TL) by performing quantitative telomere Q-FISH directly on heart sections. We found that AAV9-Tert treated hearts show a net-increase in TL in the infarct remote area (mainly formed by cardiomyocytes) compared to the empty vector group. Thus, AAV9-Tert is a potent tool to decrease short telomeres in the myocardium, and subsequently, the associated risk of heart failure in a short period of time (TL was measured 9-10 weeks after virus administration). Since short telomeres in peripheral blood lymphocytes are also proposed to have prognostic value indicating increased risk factor for CVDs, we also measured TL of peripheral blood mononuclear (PBMC) cells. We detected a modest increase in telomere length in blood cells from AAV9-Tert injected mice compared to the controls, confirming our previous observations (26). No differences in PBMC telomere length were observed between sham operated mice and those that underwent MI and received AAV9-empty or no virus, suggesting that acute MI and subsequent events such as inflammation and remodelling do not negatively impact on PBMC's TL. These findings suggest that telomerase gene therapy may have additional beneficial effects by lowering the abundance of short telomeres in the circulation, which in turn is a known risk factor for CVD.

Example 8—Telomerase Treatment Results in Increased Number of Proliferating Cardiomyocytes To study the impact of Tert treatment in apoptosis and proliferation in the heart after MI, we quantified the percentage of cells showing active caspase-3 and Ki67 positive staining, respectively, 6 weeks post MI. We found very few apoptotic cells 6 weeks post MI regardless of the treatment, in agreement with the fact that apoptosis is an early response following ischemia (33). Upon MI, we observed increased proliferation (Ki67 positive cells) in the infarct remote area and in the infarct area both in the AAV9-Tert and the AAV9-empty groups compared to the sham operated mice. However, this increase was significantly attenuated in the AAV9-Tert group compared to AAV9-empty, in line with decreased fibrotic scar formation in these mice. Interestingly, co-immunostaining using Ki67 and the cardiomyocyte marker Troponin T, showed the presence of Ki67 positive cardiomyocytes in the infarct vicinity, which were significantly increased in the Tert treated group compared to empty virus group, suggesting increased heart healing and regeneration.

Figure 4:
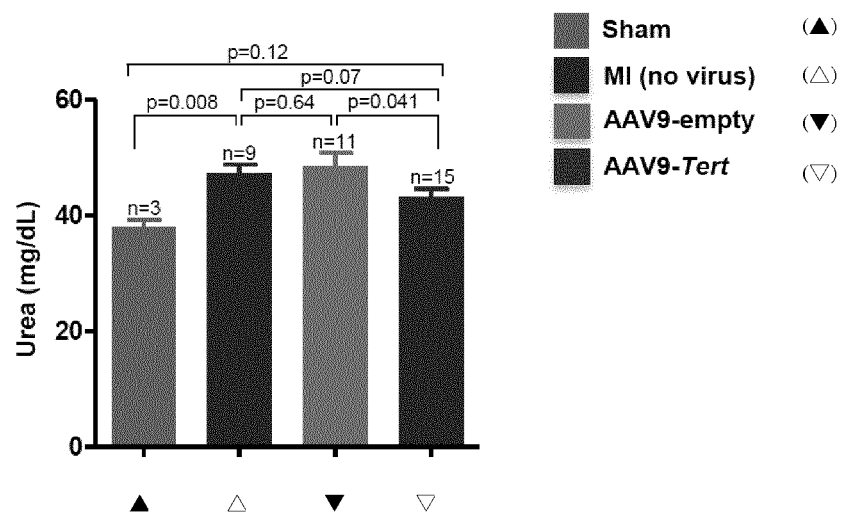
FIG. 4: Telomerase expression rescues serum parameters associated with heart failure. Serum urea concentration as a measure of renal and heart functionality was determined in the indicated groups.

Example 9—Telomerase Impacts on Metabolic and Signalling Networks Related to Cardiac Dysfunction To further understand the role of Tert in protection from acute heart failure after MI, we first studied changes in serum metabolites in the different mouse cohorts. Owing to a drastically lowered ejection fraction (FIG. 2D), MI can reduce the blood flow to the kidney and eventually induce kidney dysfunction with reduced glomerular filtration rates leading to increased urea blood levels. We found that 6 weeks after MI, serum urea levels were significantly increased in mice treated with no virus or with the empty vector, and that this was significantly rescued in the AAV9-Tert cohort (FIG. 4). A better renal function upon MI in AAV9-Tert treated mice supports our findings of improved cardiac function in these mice (FIG. 2).

Next, we performed a comprehensive serum multi-analyte profiling 6 weeks post MI encompassing various biological pathways. We found that MI resulted in significant decrease in the serum levels of factors involved in tissue remodelling such as metalloproteinases (MMP-9) and their inhibitors (TIMP-1) (34), in inflammation such as MDC (macrophage derived chemokine) or interleukin 18 (IL-18), and in the epidermal growth factor (EGF). Importantly, all of them were partially rescued in the AAV9-Tert group. Of interest, increased EGFR has been previously described as cardio protective (35).

Next, we determined the expression of the atrial natriuretic peptide (ANP), a foetal heart protein which is repressed after birth together with other foetal heart genes, but greatly increases during late stages of heart failure (2). Interestingly, ANP levels were decreased following AAV9-Tert treatment in old WT hearts (non infarcted >2 years old mice), suggesting that Tert treatment represses the pathological expression of foetal genes.

To gain further insights into the gene expression changes mediated by Tert in the heart, we performed microarray DNA analysis 6 weeks post MI, which reflect later stages of tissue repair process, including cardiac remodelling and scar formation (33). We used RNA from left ventricular heart tissue from the different groups (sham (no MI); MI+AAV9-Tert; MI+AAV9-empty). Gene set enrichment analysis (GSEA) revealed upregulation of pathways associated with inflammation, proliferation and DNA replication in the infarcted mice compared to the sham group (no MI), which were significantly rescued in AAV9-Tert treated mice compared to AAV9-empty controls. Increased inflammation is attributed to the clearance of apoptotic and necrotic cardiomyocytes upon MI, while increased proliferation is associated to repopulation of the injury zone with fibroblasts (36). Thus, the fact that Tert attenuates the expression of genes involved in inflammation and proliferation supports our functional findings that AAV9-Tert treatment is cardio protective. Moreover, we found a significant enrichment in several signatures related to remodelling of the extracellular matrix and fibroblasts dynamics (e.g. ECM, TGFβ and FGFR) in the Tert treated group compared to the empty vector controls. We confirmed some of the most differentially expressed genes within these gene sets (Fgfr3 and Bmpr1b, respectively) by qRT-22 PCR. In addition, Timp1, Thbs1 and Thbs4 (thrombospondin 1 & 4) were also differentially expressed in Tert-treated mice. Increased Timp1 expression is in agreement with higher TIMP1 protein levels in the serum from Tert treated mice. These findings are of interest given that overexpression of Timp1 has been shown to mitigate adverse myocardial remodelling and to improve cardiac function, while Thbs1 and Thbs4 are important regulators of cardiac adaptation post MI by regulating fibrosis and remodelling of the myocardium (37-39)

Neonatal mice have full regenerative potential during the first week of life, which is characterised by a well-defined gene expression signature. Thus, we next set out to address whether gene expression changes associated to Tert treatment in adult hearts were enriched in the regenerative gene expression signature described in neonatal mice. Strikingly, by comparing our expression data to genes overexpressed or underrepresented at postnatal day 1 (relative to postnatal day 10) (7), a stage at which the heart possesses full regenerative potential after MI, we found a significant enrichment in the AAV9-Tert group compared to AAV9-empty. We confirmed some of the most differentially expressed genes within these gene sets (Irf7 and Itgb6) by qRT-PCR. In summary, Tert treatment can modulate transcriptional programs that favour survival and regeneration after MI and that resemble the gene expression signature of the neonatal heart.

REFERENCES

1. Mudd, J. O. & Kass, D. A. Tackling heart failure in the twenty-first century. Nature 451, 919-928, (2008).
2. Liew, C. C. & Dzau, V. J. Molecular genetics and genomics of heart failure. Nat Rev Genet 5, 811-825, (2004).
3. Cohn, J. N., Ferrari, R. & Sharpe, N. Cardiac remodeling concepts and clinical implications: a consensus paper from an international forum on cardiac remodeling. Behalf of an International Forum on Cardiac Remodeling. J Am Coll Cardiol 35, 569-582, (2000).

4. Dominguez, L. J. et al. Ageing, lifestyle modifications, and cardiovascular disease in developing countries. J Nutr Health Aging 10, 143-149 (2006).
5. Bergmann, O. et al. Evidence for cardiomyocyte renewal in humans Science 324, 98-102, (2009).
6. Porrello, E. R. et al. Transient regenerative potential of the neonatal mouse heart. Science 331, 1078-1080, (2011).
7. Haubner, B. J. et al. Complete cardiac regeneration in a mouse model of myocardial infarction. Aging (Albany N.Y.) 4, 966-977, (2012).
8. Lopez-Otin, C., Blasco, M. A., Partridge, L., Serrano, M. & Kroemer, G. The hallmarks of aging. Cell 153, 1194-1217, (2013).
9. Boonekamp, J. J., Simons, M. J., Hemerik, L. & Verhulst, S. Telomere length behaves as biomarker of somatic redundancy rather than biological age. Aging Cell 12, 330-332, (2013).
10. Blackburn, E. H. Switching and signaling at the telomere. Cell 106, 661-673, 24 (2001).
11. de Lange, T. Shelterin: the protein complex that shapes and safeguards human telomeres. Genes Dev 19, (2005).
12. Greider, C. W. & Blackburn, E. H. Identification of a specific telomere terminal transferase activity in Tetrahymena extracts. Cell 43, 405-413, (1985).
13. Vera, E., Bernardes de Jesus, B., Foronda, M., Flores, J. M. & Blasco, M. A. The rate of increase of short telomeres predicts longevity in mammals Cell Rep 2, 732-737, (2012).
14. Flores, I. et al. The longest telomeres: a general signature of adult stem cell compartments. Genes Dev 22, 654-667, (2008).
15. Harley, C. B., Futcher, A. B. & Greider, C. W. Telomeres shorten during ageing of human fibroblasts. Nature 345, 458-460, (1990).
16. Canela, A., Vera, E., Klatt, P. & Blasco, M. A. High-throughput telomere length quantification by FISH and its application to human population studies. Proc Natl Acad Sci USA 104, 5300-5305, (2007).
17. Flores, I., Cayuela, M. L. & Blasco, M. A. Effects of telomerase and telomere length on epidermal stem cell behavior. Science 309, (2005).
18. Heidinger, B. J. et al. Telomere length in early life predicts lifespan. Proc Natl Acad Sci USA 109, 1743-1748, (2012).
19. Leri, A. et al. Ablation of telomerase and telomere loss leads to cardiac dilatation and heart failure associated with p53 upregulation. EMBO J 22, 131-139, (2003).
20. de Jesus, B. B. & Blasco, M. A. Assessing cell and organ senescence biomarkers. Circ Res 111, 97-109, (2012).
21. De Meyer, T., Rietzschel, E. R., De Buyzere, M. L., Van Criekinge, W. & Bekaert, S. Telomere length and cardiovascular aging: the means to the ends? Ageing Res Rev 10, 297-303, (2011).
22. Blasco, M. A., Funk, W., Villeponteau, B. & Greider, C. W. Functional characterization and developmental regulation of mouse telomerase RNA Science 269, 1267-1270 (1995).
23. Borges, A. & Liew, C. C. Telomerase activity during cardiac development. J Mol Cell Cardiol 29, 2717-2724, (1997).
24. Tomas-Loba, A. et al. Telomerase reverse transcriptase delays aging in cancer-resistant mice. Cell 135, 609-622, (2008).
25. Oh, H. et al. Telomerase reverse transcriptase promotes cardiac muscle cell proliferation, hypertrophy, and survival. Proc Natl Acad Sci USA 98, (2001).
26. Bernardes de Jesus, B. et al. Telomerase gene therapy in adult and old mice delays aging and increases longevity without increasing cancer. EMBO Mol 30 Med 4, 1-14, (2012).
27. Park, J. I. et al. Telomerase modulates Wnt signalling by association with target gene chromatin Nature 460, 66-72, (2009).
28. Gao, G. P. et al. Novel adeno-associated viruses from rhesus monkeys as vectors for human gene therapy. Proc Natl Acad Sci USA 99, (2002).
29. Zincarelli, C., Soltys, S., Rengo, G. & Rabinowitz, J. E. Analysis of AAV 3 serotypes 1-9 mediated gene expression and tropism in mice after systemic injection. Mol Ther 16, (2008).
30. van den Borne, S. W. et al. Mouse strain determines the outcome of wound healing after myocardial infarction. Cardiovasc Res 84, 273-282, (2009).
31. Konkalmatt, P. R. et al. Cardiac-selective expression of extracellular superoxide dismutase after systemic injection of adeno-associated virus 9 protects the heart against post-myocardial infarction left ventricular remodeling. Circ Cardiovasc Imaging 6, 478-486 (2013).
32. Stegger, L. et al. Accurate noninvasive measurement of infarct size in mice with high-resolution PET. J Nucl Med 47, 1837-1844, (2006).
33. Ertl, G. & Frantz, S. Healing after myocardial infarction. Cardiovasc Res 66, 14 22-32, (2005).
34. Brew, K., Dinakarpandian, D. & Nagase, H. Tissue inhibitors of metalloproteinases: evolution, structure and function. Biochim Biophys Acta 17 1477, 267-283, (2000).
35. Noma, T. et al. Beta-arrestin-mediated beta1-adrenergic receptor transactivation of the EGFR confers cardioprotection. J Clin Invest 117, 2445-2458, (2007).
36. Dobaczewski, M., Gonzalez-Quesada, C. & Frangogiannis, N. G. The extracellular matrix as a modulator of the inflammatory and reparative response following myocardial infarction. J Mol Cell Cardiol 48, 504-511, 24 (2010).
37. Frolova, E. G. et al. Thrombospondin-4 regulates fibrosis and remodeling of the myocardium in response to pressure overload. FASEB J 26, 2363-2373, (2012).
38. Frangogiannis, N. G. et al. Critical role of endogenous thrombospondin-1 in preventing expansion of healing myocardial infarcts. Circulation 111, 2935-2942, (2005).
39. Frangogiannis, N. G. Matricellular proteins in cardiac adaptation and disease. Physiol Rev 92, 635-688, (2012).
40. Jaskelioff, M. et al. Telomerase reactivation reverses tissue degeneration in aged telomerase-deficient mice. Nature 469, 102-106, (2011).
41. Richardson, G. D. et al. Telomerase expression in the mammalian heart. FASEB J 26, 4832-4840, (2012).
42. Lowes, B. D. et al. Myocardial gene expression in dilated cardiomyopathy treated with beta-blocking agents. N Engl J Med 346, 1357-1365, (2002).
43. Dobaczewski, M., Chen, W. & Frangogiannis, N. G. Transforming growth factor (TGF)-beta signaling in cardiac remodeling. J Mol Cell Cardiol 51, 600-606, (2011).
44. Jopling, C. et al. Zebrafish heart regeneration occurs by cardiomyocyte dedifferentiation and proliferation. Nature 25, 606-609, (2010).
45. Anversa, P. & Kajstura, J. Ventricular myocytes are not terminally differentiated in the adult mammalian heart. Circ Res 83, 1-14 (1998).
46. Beltrami, A. P. et al. Evidence that human cardiac myocytes divide after myocardial infarction. N Engl J Med 344, 1750-1757, (2001).

47. Glass, C. & Singla, D. K. Overexpression of TIMP-1 in embryonic stem cells attenuates adverse cardiac remodeling following myocardial infarction. Cell Transplant 21, 1931-1944, (2012).
48. Matsushita, T. et al. Adeno-associated virus vectors can be efficiently produced without helper virus. Gene Ther 5, 938-945, (1998).
49. Ayuso, E. et al. High AAV vector purity results in serotype- and tissue-independent enhancement of transduction efficiency. Gene Ther 17, 503-510, (2010).
50. Blasco, M. A., Rizen, M., Greider, C. W. & Hanahan, D. Differential regulation of telomerase activity and telomerase RNA during multi-stage tumorigenesis. Nat Genet 12, 200-204, (1996).
51. Zincarelli, C., Soltys, S., Rengo, G. & Rabinowitz, J. E. Analysis of AAV serotypes 1-9 mediated gene expression and tropism in mice after systemic injection. Mol Ther 16, (2008).
52. Korf-Klingebiel, M. et al. Conditional transgenic expression of fibroblast growth factor 9 in the adult mouse heart reduces heart failure mortality after myocardial infarction. Circulation 123, 504-514, (2011).
53. Mulero, F., Donate, L. E. & Serrano, M. in Current Protocols in Mouse Biology (John Wiley & Sons, Inc., 2011).
54. Vera, E., Bernardes de Jesus, B., Foronda, M., Flores, J. M. & Blasco, M. A. The rate of increase of short telomeres predicts longevity in mammals Cell Rep 2, 732-737, (2012).
55. Bernardes de Jesus, B. et al. Telomerase gene therapy in adult and old mice delays aging and increases longevity without increasing cancer. EMBO Mol Med 4, 1-14, (2012).
56. Canela, A., Klatt, P. & Blasco, M. A. Telomere length analysis. Methods Mol Biol 371, 45-72, (2007).
57. Tomas-Loba, A., Bernardes de Jesus, B., Mato, J. M. & Blasco, M. A. A metabolic signature predicts biological age in mice. Aging Cell 12, 93-101, (2013).
58. Martinez, P. et al. RAPT protects from obesity through its extratelomeric role regulating gene expression. Cell Rep 3, 2059-2074, (2013).
59. Smyth, G. K., Michaud, J. & Scott, H. S. Use of within-array replicate spots for assessing differential expression in microarray experiments. Bioinformatics 2 21, 2067-2075, (2005).
60. Subramanian, A. et al. Gene set enrichment analysis: a knowledge-based approach for interpreting genome-wide expression profiles. Proc Natl Acad 5 Sci USA 102, 15545-15550, (2005).
61. Blasco, M. Telomere length, stem cells and aging. Nat Chem Biol. 3, 640-649, (2007).
62. Mcilrath, J. et al. Telomere length abnormalities in mammalian radiosensitive cells. Cancer Res 61: 912-915, (2001).
63. Brouilette, S. W. et al. Telomere length, risk of coronary heart disease, and statin treatment in the West of Scotland Primary Prevention Study: a nested case-control study. Lancet 369: 107-114 (2007).
64. Moslehi, J., R. A. Depinho & E. Sahin, Telomeres and mitochondria in the aging heart. Circ Res 110: 1226-1237 (2012).
65. Blasco, M. A., H. W. Lee, et al. Telomere shortening and tumour formation by mouse cells lacking telomerase RNA. Cell 91(1): 25-34 (1997).
66. Gonzalez-Suarez, E., E. Samper, et al. (2001). "Increased epidermal tumours and increased skin wound healing in transgenic mice overexpressing the catalytic subunit of telomerase, mTERT, in basal keratinocytes." EMBO J 20(11): 2619-30 (2001).
67. Merten, O. W., C. Geny-Fiamma, et al. Current issues in adeno-associated viral vector production. Gene Ther 12 Suppl 1: S51-61 (2005).
68. Buning, H., L. Perabo, et al. Recent developments in adeno-associated virus vector technology. J Gene Med 10(7): 717-33 (2008).
69. Niemeyer G. P. et al. Long-term correction of inhibitor-prone hemophilia B dogs treated with liver-directed AAV2-mediated factor IX gene therapy. Blood 113(4): 797-806. (2009).
70. Mas A., et al. Reversal of type I diabetes by engineering a glucose sensor in skeletal muscle. Diabetes 55: 1546-1553 (2006).
71. Jiang, H., et al. Multiyear therapeutic benefit of AAV serotypes 2, 6, and 8 delivering factor VIII to hemophilia A mice and dogs. Blood. 108(1):107-15. (2006).
72. Ghosh, A., et al. Efficient Whole-body Transduction with Trans-splicing Adeno-associated Viral Vectors. Mol Therapy 15(4): 750-755. (2007).
73. Tafuro S., et al. Inducible adeno-associated virus vectors promote functional angiogenesis in adult organisms via regulated vascular endothelial growth factor expression. Cardiovasc Res 83(4):663-71 (2009).
74. Manno, C. S. et al. Successful transduction of liver in hemophilia by AAV-Factor IX and limitations imposed by the host immune response. Nature Med. 12(3): 342-347. (2006).
75. Stroes E S, et al. Intramuscular administration of AAV1-lipoprotein lipase S447X lowers triglycerides in lipoprotein lipase-deficient patients. Arterioscler Thromb Vasc Biol. 12:2303-4. (2008)
76. Kaplitt, M. G. et al. Safety and tolerability of gene therapy with an adeno-associated virus (AAV) borne GAD gene for Parkinson's disease: an open label, phase I trial. The Lancet, 369 (9579):2097-2105, (2007).
77. Maguire A. M., et al. Safety and efficacy of gene transfer for Leber's congenital amaurosis. N Engl J Med. 358(21): 2240-8. (2008).
78. Bainbridge, J. W B., et al. Effect of Gene Therapy on Visual Function in Leber's Congenital Amaurosis. N Engl J Med. 358:2231-2239. (2008).
79. Mingozzi, F. et al. CD8+ T-cell responses to adeno-associated virus capsid in humans. Nature Med. 13, 419-422 (2007).
80. Brantly, M. L., et al. Sustained transgene expression despite T lymphocyte responses in a clinical trial of rAAV1-AAT gene therapy. Proc Natl Acad Sci USA. 106:16363-16368. (2009).
81. Mingozzi F, et al. AAV-1-mediated gene transfer to skeletal muscle in humans results in dose-dependent activation of capsid-specific T cells. Blood. 114:2077-2086. (2009).
82. Simonelli, F., et al. Therapy for Leber's Congenital Amaurosis is Safe and Effective Through 1.5 Years After Vector Administration. Mol Ther. 18(3): 643-650. (2010).
83. Inagaki, K., S. Fuess, et al. Robust systemic transduction with AAV9 vectors in mice: efficient global cardiac gene transfer superior to that of AAV8. Mol Ther 14(1): 45-53. (2006).
84. Foust, K. D. et al. Intravascular AAV9 preferentially targets neonatal neurons and adult astrocytes. Nature Biotechnology, 27:59-65. (2009).
85. Duque S., et al. Intravenous administration of self-complementary AAV9 enables transgene delivery to adult motor neurons. Molecular Therapy 17(7): 1187-1196. (2009).
86. Samper E., et al. Restoration of telomerase activity rescues chromosomal instability and premature aging in Terc−/− mice with short telomeres. EMBO Rep. 2(9):800-7. (2001).

We claim:

1. A method of treating a condition associated with myocardial infarction, the method comprising:
 administering to a subject in need thereof a non-integrative viral vector comprising a coding sequence for telomerase reverse transcriptase (TERT), wherein the condition associated with myocardial infarction is selected from the group consisting of a myocardial infarction, tissue damage resulting from myocardial infarction, fibrosis of the myocardium resulting from myocardial infarction, and reduced cardiac function resulting from myocardial infarction, and wherein the method results in the transduction of heart cells.

2. The method of claim 1, wherein the subject has previously suffered a myocardial infarction event.

3. The method of claim 1, wherein TERT is encoded by a nucleic acid sequence comprising the sequence of SEQ ID NO: 1 or SEQ ID NO: 3.

4. The method of claim 1, wherein TERT comprises the amino acid sequence of SEQ ID NO:2 or SEQ ID NO: 4.

5. The method of claim 1, wherein the nucleic acid sequence encoding TERT is operably linked to a regulatory sequence that drives the expression of the coding sequence.

6. The method of claim 1, wherein the non-integrative viral vector is an adeno-associated virus-based vector.

7. The method of claim 1, wherein the non-integrative viral vector is an adeno-associated virus-based vector whose capsid is derived from the serotype 9 adeno-associated virus (AAV9).

8. The method of claim 7, wherein the coding sequence is packaged in the capsid and is flanked at both ends by the internal terminal repeats of the serotype 2 adeno-associated virus.

9. The method of claim 1, wherein the non-integrative viral vector comprises a regulatory sequence encoding a constitutive promoter.

10. The method of claim 9, wherein the constitutive promoter is the cytomegalovirus (CMV) promoter.

11. The method of claim 1, wherein the non-integrative viral vector is administered directly to the cardiac tissue.

12. The method of claim 1, wherein the non-integrative viral vector is administered within twelve hours, twenty-four hours, thirty-six hours, forty-eight hours, sixty hours, seventy-two hours, or eighty-four hours after the myocardial infarction.

* * * * *

SEQUENCE LISTING

<160> NUMBER OF SEQ ID NOS: 22

<210> SEQ ID NO 1
<211> LENGTH: 4018
<212> TYPE: DNA
<213> ORGANISM: Homo sapiens

<400> SEQUENCE: 1

| | | | | | |
|---|---|---|---|---|---|
| caggcagcgc | tgcgtcctgc | tgcgcacgtg | ggaagccctg | gccccggcca | ccccgcgat | 60 |
| gccgcgcgct | ccccgctgcc | gagccgtgcg | ctccctgctg | cgcagccact | accgcgaggt | 120 |
| gctgccgctg | gccacgttcg | tgcggcgcct | ggggccccag | ggctggcggc | tggtgcagcg | 180 |
| cggggacccg | gcggctttcc | gcgcgctggt | ggcccagtgc | ctggtgtgcg | tgccctggga | 240 |
| cgcacggccg | ccccccgccg | cccctccttt | ccgccaggtg | tcctgcctga | aggagctggt | 300 |
| ggcccgagtg | ctgcagaggc | tgtgcgagcg | cggcgcgaag | aacgtgctgg | ccttcggctt | 360 |
| cgcgctgctg | gacggggccc | gcgggggccc | cccgaggcc | ttcaccacca | gcgtgcgcag | 420 |
| ctacctgccc | aacacggtga | ccgacgcact | gcggggagc | ggggcgtggg | ggctgctgct | 480 |
| gcgccgcgtg | ggcgacgacg | tgctggttca | cctgctggca | cgctgcgcgc | tctttgtgct | 540 |
| ggtggctccc | agctgcgcct | accaggtgtg | cgggccgccg | ctgtaccagc | tcggcgctgc | 600 |
| cactcaggcc | cggccccgc | cacacgctag | tggaccccga | aggcgtctgg | gatgcgaacg | 660 |
| ggcctggaac | catagcgtca | gggaggccgg | ggtcccctg | ggcctgccag | ccccgggtgc | 720 |
| gaggaggcgc | gggggcagtg | ccagccgaag | tctgccgttg | cccaagaggc | caggcgtgg | 780 |
| cgctgcccct | gagccggagc | ggacgcccgt | gggcagggg | tcctgggccc | acccgggcag | 840 |
| gacgcgtgga | ccgagtgacc | gtggtttctg | tgtggtgtca | cctgccagac | ccgccgaaga | 900 |
| agccacctct | ttggagggtg | cgctctctgg | cacgcgccac | tcccacccat | ccgtgggccg | 960 |
| ccagcaccac | gcgggccccc | catccacatc | gcggccacca | cgtccctggg | acacgccttg | 1020 |
| tccccggtg | tacgccgaga | ccaagcactt | cctctactcc | tcaggcgaca | aggagcagct | 1080 |
| gcggcccctcc | ttcctactca | gctctctgag | gcccagcctg | actggcgctc | ggaggctcgt | 1140 |
| ggagaccatc | tttctggggtt | ccaggccctg | gatgccaggg | actcccgca | ggttgccccg | 1200 |
| cctgccccag | cgctactggc | aaatgcggcc | cctgtttctg | gagctgcttg | ggaaccacgc | 1260 |
| gcagtgcccc | tacggggtgc | tcctcaagac | gcactgcccg | ctgcgagctg | cggtcacccc | 1320 |
| agcagccggt | gtctgtgccc | gggagaagcc | ccagggctct | gtggcggccc | cgaggagga | 1380 |
| ggacacagac | ccccgtcgcc | tggtgcagct | gctccgccag | cacagcagcc | cctggcaggt | 1440 |
| gtacggcttc | gtgcgggcct | gcctgcgccg | gctggtgccc | ccaggcctct | ggggctccag | 1500 |
| gcacaacgaa | cgccgcttcc | tcaggaacac | caagaagttc | atctcccctgg | ggaagcatgc | 1560 |
| caagctctcg | ctgcaggagc | tgacgtggaa | gatgagcgtg | cgggactgcg | cttggctgcg | 1620 |
| caggagccca | gggttggct | gtgttccggc | cgcagagcac | cgtctgcgtg | aggagatcct | 1680 |
| ggccaagttc | ctgcactggc | tgatgagtgt | gtacgtcgtc | gagctgctca | ggtctttctt | 1740 |
| ttatgtcacg | gagaccacgt | ttcaaaagaa | caggctcttt | ttctaccgga | agagtgtctg | 1800 |
| gagcaagttg | caaagcattg | gaatcagaca | gcacttgaag | agggtgcagc | tgcgggagct | 1860 |
| gtcggaagca | gaggtcaggc | agcatcggga | agccaggccc | gccctgctga | cgtccagact | 1920 |
| ccgcttcatc | cccaagcctg | acgggctgcg | gccgattgtg | aacatggact | acgtcgtggg | 1980 |
| agccagaacg | ttccgcagag | aaaagagggc | cgagcgtctc | acctcgaggg | tgaaggcact | 2040 |
| gttcagcgtg | ctcaactacg | agcgggcgcg | gcgccccggc | ctcctgggcg | cctctgtgct | 2100 |

```
gggcctggac gatatccaca gggcctggcg caccttcgtg ctgcgtgtgc gggcccagga    2160
cccgccgcct gagctgtact ttgtcaaggt ggatgtgacg ggcgcgtacg acaccatccc    2220
ccaggacagg ctcacggagg tcatcgccag catcatcaaa ccccagaaca cgtactgcgt    2280
gcgtcggtat gccgtggtcc agaaggccgc ccatgggcac gtccgcaagg ccttcaagag    2340
ccacgtctct accttgacag acctccagcc gtacatgcga cagttcgtgg ctcacctgca    2400
ggagaccagc ccgctgaggg atgccgtcgt catcgagcag agctcctccc tgaatgaggc    2460
cagcagtggc ctcttcgacg tcttcctacg cttcatgtgc caccacgccg tgcgcatcag    2520
gggcaagtcc tacgtccagt gccaggggat cccgcagggc tccatcctct ccacgctgct    2580
ctgcagcctg tgctacggcg acatggagaa caagctgttt gcgggattc ggcgggacgg    2640
gctgctcctg cgtttggtgg atgatttctt gttggtgaca cctcacctca cccacgcgaa    2700
aaccttcctc aggaccctgg tccgaggtgt ccctgagtat ggctgcgtgg tgaacttgcg    2760
gaagacagtg gtgaacttcc ctgtagaaga cgaggccctg ggtggcacgg cttttgttca    2820
gatgccggcc cacggcctat tccctggtg cggcctgctg ctggataccc ggaccctgga    2880
ggtgcagagc gactactcca gctatgcccg gacctccatc agagccagtc tcaccttcaa    2940
ccgcggcttc aaggctggga ggaacatgcg tcgcaaactc tttggggtct gcggctgaa    3000
gtgtcacagc tgtttctgg atttgcaggt gaacagcctc cagacggtgt gcaccaacat    3060
ctacaagatc ctcctgctgc aggcgtacag gtttcacgca tgtgtgctgc agctcccatt    3120
tcatcagcaa gtttggaaga cccacatt tttcctgcgc gtcatctctg acacggcctc    3180
cctctgctac tccatcctga agccaagaa cgcagggatg tcgctggggg ccaagggcgc    3240
cgccggccct ctgccctccg aggccgtgca gtggctgtgc caccaagcat tcctgctcaa    3300
gctgactcga caccgtgtca cctacgtgcc actcctgggg tcactcagga cagcccagac    3360
gcagctgagt cggaagctcc cggggacgac gctgactgcc ctggaggccg cagccaaccc    3420
ggcactgccc tcagacttca agaccatcct ggactgatgg ccacccgccc acagccaggc    3480
cgagagcaga caccagcagc cctgtcacgc cgggctctac gtcccaggga gggaggggcg    3540
gcccacaccc aggcccgcac cgctgggagt ctgaggcctg agtgagtgtt tggccgaggc    3600
ctgcatgtcc ggctgaaggc tgagtgtccg gctgaggcct gagcgagtgt ccagccaagg    3660
gctgagtgtc cagcacacct gccgtcttca cttccccaca ggctggcgct cggctccacc    3720
ccagggccag ctttcctca ccaggagccc ggcttccact ccccacatag aatagtcca    3780
tccccagatt cgccattgtt caccctcgc cctgccctcc tttgccttcc accccacca    3840
tccaggtgga gaccctgaga aggaccctgg gagctctggg aatttggagt gaccaaaggt    3900
gtgccctgta cacaggcgag gacctgcac ctggatgggg gtccctgtgg gtcaaattgg    3960
ggggaggtgc tgtgggagta aaatactgaa tatatgagtt tttcagtttt gaaaaaaa    4018
```

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

```
Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
 50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
                100                 105                 110

Glu Ala Phe Thr Thr Ser Val Arg Ser Tyr Leu Pro Asn Thr Val Thr
                115                 120                 125

Asp Ala Leu Arg Gly Ser Gly Ala Trp Gly Leu Leu Leu Arg Arg Val
130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
                180                 185                 190

Pro Arg Arg Arg Leu Gly Cys Glu Arg Ala Trp Asn His Ser Val Arg
                195                 200                 205

Glu Ala Gly Val Pro Leu Gly Leu Pro Ala Pro Gly Ala Arg Arg Arg
                210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
                260                 265                 270

Val Ser Pro Ala Arg Pro Ala Glu Glu Ala Thr Ser Leu Glu Gly Ala
                275                 280                 285

Leu Ser Gly Thr Arg His Ser His Pro Ser Val Gly Arg Gln His His
                290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
                355                 360                 365

Arg Pro Trp Met Pro Gly Thr Pro Arg Arg Leu Pro Arg Leu Pro Gln
                370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Glu Asp Thr Asp Pro Arg Arg Leu
                435                 440                 445

Val Gln Leu Leu Arg Gln His Ser Ser Pro Trp Gln Val Tyr Gly Phe
```

```
                450             455             460
Val Arg Ala Cys Leu Arg Arg Leu Val Pro Pro Gly Leu Trp Gly Ser
465                     470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880
```

Lys Thr Phe Leu Arg Thr Leu Val Arg Gly Val Pro Glu Tyr Gly Cys
            885                 890                 895
Val Val Asn Leu Arg Lys Thr Val Val Asn Phe Pro Val Glu Asp Glu
            900                 905                 910
Ala Leu Gly Gly Thr Ala Phe Val Gln Met Pro Ala His Gly Leu Phe
        915                 920                 925
Pro Trp Cys Gly Leu Leu Leu Asp Thr Arg Thr Leu Glu Val Gln Ser
930                 935                 940
Asp Tyr Ser Ser Tyr Ala Arg Thr Ser Ile Arg Ala Ser Leu Thr Phe
945                 950                 955                 960
Asn Arg Gly Phe Lys Ala Gly Arg Asn Met Arg Arg Lys Leu Phe Gly
            965                 970                 975
Val Leu Arg Leu Lys Cys His Ser Leu Phe Leu Asp Leu Gln Val Asn
        980                 985                 990
Ser Leu Gln Thr Val Cys Thr Asn Ile Tyr Lys Ile Leu Leu Leu Gln
        995                 1000                1005
Ala Tyr Arg Phe His Ala Cys Val Leu Gln Leu Pro Phe His Gln Gln
    1010                1015                1020
Val Trp Lys Asn Pro Thr Phe Phe Leu Arg Val Ile Ser Asp Thr Ala
1025                1030                1035                1040
Ser Leu Cys Tyr Ser Ile Leu Lys Ala Lys Asn Ala Gly Met Ser Leu
            1045                1050                1055
Gly Ala Lys Gly Ala Ala Gly Pro Leu Pro Ser Glu Ala Val Gln Trp
            1060                1065                1070
Leu Cys His Gln Ala Phe Leu Lys Leu Thr Arg His Arg Val Thr
            1075                1080                1085
Tyr Val Pro Leu Leu Gly Ser Leu Arg Thr Ala Gln Thr Gln Leu Ser
        1090                1095                1100
Arg Lys Leu Pro Gly Thr Thr Leu Thr Ala Leu Glu Ala Ala Ala Asn
1105                1110                1115                1120
Pro Ala Leu Pro Ser Asp Phe Lys Thr Ile Leu Asp
            1125                1130

<210> SEQ ID NO 3
<211> LENGTH: 3982
<212> TYPE: DNA
<213> ORGANISM: Homo sapiens

<400> SEQUENCE: 3
caggcagcgc tgcgtcctgc tgcgcacgtg ggaagccctg ccccggcca ccccgcgat      60 gccgcgcgct ccccgctgcc gagccgtgcg ctccctgctg cgcagccact accgcgaggt    120
gctgccgctg ccacgttcg tgcggcgcct ggggccccag ggctggcggc tggtgcagcg    180
cggggacccg gcggctttcc gcgcgctggt ggcccagtgc ctggtgtgcg tgccctggga    240
cgcacggccg ccccccgccg cccctcctt ccgccaggtg tcctgcctga aggagctggt    300
ggcccgagtg ctgcagaggc tgtgcgagcg cggcgcgaag aacgtgctgg ccttcggctt    360
cgcgctgctg acggggcccg cggggggccc ccccgaggcc ttcaccacca gcgtgcgcag    420
ctacctgccc aacacggtga ccgacgcact gcggggggagc ggggcgtggg ggctgctgct    480
gcgccgcgtg ggcgacgacg tgctggttca cctgctggca cgctgcgcgc tctttgtgct    540
ggtggctccc agctgcgcct accaggtgtg cgggccgccg ctgtaccagc tcggcgctgc    600
cactcaggcc cggccccgc acacgctag tggaccccga aggcgtctgg gatgcgaacg      660

-continued

```
ggcctggaac catagcgtca gggaggccgg ggtcccsctg ggcctgccag ccccgggtgc    720
gaggaggcgc gggggcagtg ccagccgaag tctgccgttg cccaagaggc ccaggcgtgg    780
cgctgcccct gagccggagc ggacgcccgt tgggcagggg tcctgggccc acccgggcag    840
gacgcgtgga ccgagtgacc gtggtttctg tgtggtgtca cctgccagac ccgccgaaga    900
agccacctct ttggagggtg cgctctctgg cacgcgccac tcccacccat ccgtgggccg    960
ccagcaccac gcgggccccc catccacatc gcggccacca cgtccctggg acacgccttg   1020
tcccccggtg tacgccgaga ccaagcactt cctctactcc tcaggcgaca aggagcagct   1080
gcggccctcc ttcctactca gctctctgag gcccagcctg actggcgctc ggaggctcgt   1140
ggagaccatc tttctgggtt ccaggccctg gatgccaggg actcccgca ggttgccccg    1200 cctgccccag cgctactggc aaatgcggcc cctgtttctg gagctgcttg gaaccacgc    1260 gcagtgcccc tacggggtgc tcctcaagac gcactgcccg ctgcgagctg cggtcacccc   1320
agcagccggt gtctgtgccc gggagaagcc ccagggctct gtggcggccc ccgaggagga   1380
ggacacagac ccccgtcgcc tggtgcagct gctccgccag cacagcagcc cctggcaggt   1440
gtacggcttc gtgcgggcct gcctgcgccg gctggtgccc ccaggcctct ggggctccag   1500
gcacaacgaa cgccgcttcc tcaggaacac caagaagttc atctccctgg ggaagcatgc   1560
caagctctcg ctgcaggagc tgacgtggaa gatgagcgtg cgggactgcg cttggctgcg   1620
caggagccca ggggttggct gtgttccggc cgcagagcac cgtctgcgtg aggagatcct   1680
ggccaagttc ctgcactggc tgatgagtgt gtacgtcgtc gagctgctca ggtctttctt   1740
ttatgtcacg gagaccacgt ttcaaaagaa caggctcttt ttctaccgga agagtgtctg   1800
gagcaagttg caaagcattg aatcagaca gcacttgaag agggtgcagc tgcgggagct   1860
gtcggaagca gaggtcaggc agcatcggga agccaggccc gccctgctga cgtccagact   1920
ccgcttcatc cccaagcctg acgggctgcg gccgattgtg aacatggact acgtcgtggg   1980
agccagaact tccgcagag aaaagagggc cgagcgtctc acctcgaggg tgaaggcact   2040
gttcagcgtg ctcaactacg agcgggcgcg gcgccccggc ctcctgggcg cctctgtgct   2100
gggcctggac gatatccaca gggcctggcg caccttcgtg ctgcgtgtgc gggcccagga   2160
cccgccgcct gagctgtact ttgtcaagga caggctcacg gaggtcatcg ccagcatcat   2220
caaaccccag aacacgtact gcgtgcgtcg gtatgccgtg gtccagaagg ccgcccatgg   2280
gcacgtccgc aaggccttca agagccacgt ctctaccttg acagacctcc agccgtacat   2340
gcgacagttc gtggctcacc tgcaggagac cagcccgctg agggatgccg tcgtcatcga   2400
gcagagctcc tccctgaatg aggccagcag tggcctcttc gacgtcttcc tacgcttcat   2460
gtgccaccac gccgtgcgca tcaggggcaa gtcctacgtc cagtgccagg ggatcccgca   2520
gggctccatc ctctccacgc tgctctgcag cctgtgctac ggcgacatgg agaacaagct   2580
gtttgcgggg attcggcggg acgggctgct cctgcgtttg gtggatgatt tcttgttggt   2640
gacacctcac ctcacccacg cgaaaaactt cctcaggacc ctggtccgag tgtccctga   2700 gtatggctgc gtggtgaact tgcggaagac agtggtgaac ttccctgtag aagacgaggc   2760
cctgggtggc acggcttttg ttcagatgcc ggccacggc ctattcccct ggtgcggcct    2820
gctgctggat acccggaccc tggaggtgca gagcgactac tccagctatg cccggacctc   2880
catcagagcc agtctcacct tcaaccgcgg cttcaaggct gggaggaaca tgcgtcgcaa   2940
actctttggg gtcttgcggc tgaagtgtca cagcctgttt ctggatttgc aggtgaacag   3000
cctccagacg gtgtgcacca acatctacaa gatcctcctg ctgcaggcgt acaggtttca   3060
```

```
cgcatgtgtg ctgcagctcc catttcatca gcaagtttgg aagaacccca cattttcct    3120
gcgcgtcatc tctgacacgg cctccctctg ctactccatc ctgaaagcca agaacgcagg    3180
gatgtcgctg ggggccaagg gcgccgccgg ccctctgccc tccgaggccg tgcagtggct    3240
gtgccaccaa gcattcctgc tcaagctgac tcgacaccgt gtcacctacg tgccactcct    3300
ggggtcactc aggacagccc agacgcagct gagtcggaag ctcccgggga cgacgctgac    3360
tgccctggag gccgcagcca acccggcact gccctcagac ttcaagacca tcctggactg    3420
atggccaccc gcccacagcc aggccgagag cagacaccag cagccctgtc acgccgggct    3480
ctacgtccca gggagggagg ggcggcccac acccaggccc gcaccgctgg gagtctgagg    3540
cctgagtgag tgtttggccg aggcctgcat gtccggctga aggctgagtg tccggctgag    3600
gcctgagcga gtgtccagcc aagggctgag tgtccagcac acctgccgtc ttcacttccc    3660
cacaggctgg cgctcggctc caccccaggg ccagcttttc ctcaccagga gcccggcttc    3720
cactccccac ataggaatag tccatcccca gattcgccat tgttcacccc tcgccctgcc    3780
ctcctttgcc ttccaccccc accatccagg tggagaccct gagaaggacc ctgggagctc    3840
tgggaatttg gagtgaccaa aggtgtgccc tgtacacagg cgaggaccct gcacctggat    3900
ggggggtccct gtgggtcaaa ttggggggag gtgctgtggg agtaaaatac tgaatatatg    3960
agttttcag ttttgaaaaa aa                                               3982
```

<210> SEQ ID NO 4
<211> LENGTH: 1120
<212> TYPE: PRT
<213> ORGANISM: Homo sapiens

<400> SEQUENCE: 4

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205
```

-continued

```
Glu Ala Gly Val Pro Leu Gly Leu Pro Ala Pro Gly Ala Arg Arg
    210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
                245                 250                 255
Ala His Pro Gly Arg Thr Arg Gly Pro Ser Asp Arg Gly Phe Cys Val
                260                 265                 270
Val Ser Pro Ala Arg Pro Ala Glu Glu Ala Thr Ser Leu Glu Gly Ala
        275                 280                 285
Leu Ser Gly Thr Arg His Ser His Pro Ser Val Gly Arg Gln His His
    290                 295                 300
Ala Gly Pro Pro Ser Thr Ser Arg Pro Pro Arg Pro Trp Asp Thr Pro
305                 310                 315                 320
Cys Pro Pro Val Tyr Ala Glu Thr Lys His Phe Leu Tyr Ser Ser Gly
                325                 330                 335
Asp Lys Glu Gln Leu Arg Pro Ser Phe Leu Leu Ser Ser Leu Arg Pro
                340                 345                 350
Ser Leu Thr Gly Ala Arg Arg Leu Val Glu Thr Ile Phe Leu Gly Ser
    355                 360                 365
Arg Pro Trp Met Pro Gly Thr Pro Arg Arg Leu Pro Arg Leu Pro Gln
    370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
                420                 425                 430
Gly Ser Val Ala Ala Pro Glu Glu Asp Thr Asp Pro Arg Arg Leu
            435                 440                 445
Val Gln Leu Leu Arg Gln His Ser Ser Pro Trp Gln Val Tyr Gly Phe
    450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
                500                 505                 510
Ser Val Arg Asp Cys Ala Trp Leu Arg Arg Ser Pro Gly Val Gly Cys
        515                 520                 525
Val Pro Ala Ala Glu His Arg Leu Arg Glu Ile Leu Ala Lys Phe
    530                 535                 540
Leu His Trp Leu Met Ser Val Tyr Val Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
        595                 600                 605
His Arg Glu Ala Arg Pro Ala Leu Leu Thr Ser Arg Leu Arg Phe Ile
    610                 615                 620
```

```
Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Gly Leu Asp Asp Ile His Arg
        675                 680                 685

Ala Trp Arg Thr Phe Val Leu Arg Val Arg Ala Gln Asp Pro Pro
690                 695                 700

Glu Leu Tyr Phe Val Lys Asp Arg Leu Thr Glu Val Ile Ala Ser Ile
705                 710                 715                 720

Ile Lys Pro Gln Asn Thr Tyr Cys Val Arg Arg Tyr Ala Val Val Gln
                725                 730                 735

Lys Ala Ala His Gly His Val Arg Lys Ala Phe Lys Ser His Val Ser
                740                 745                 750

Thr Leu Thr Asp Leu Gln Pro Tyr Met Arg Gln Phe Val Ala His Leu
            755                 760                 765

Gln Glu Thr Ser Pro Leu Arg Asp Ala Val Val Ile Glu Gln Ser Ser
770                 775                 780

Ser Leu Asn Glu Ala Ser Ser Gly Leu Phe Asp Val Phe Leu Arg Phe
785                 790                 795                 800

Met Cys His His Ala Val Arg Ile Arg Gly Lys Ser Tyr Val Gln Cys
                805                 810                 815

Gln Gly Ile Pro Gln Gly Ser Ile Leu Ser Thr Leu Leu Cys Ser Leu
                820                 825                 830

Cys Tyr Gly Asp Met Glu Asn Lys Leu Phe Ala Gly Ile Arg Arg Asp
            835                 840                 845

Gly Leu Leu Leu Arg Leu Val Asp Asp Phe Leu Leu Val Thr Pro His
850                 855                 860

Leu Thr His Ala Lys Thr Phe Leu Arg Thr Leu Val Arg Gly Val Pro
865                 870                 875                 880

Glu Tyr Gly Cys Val Val Asn Leu Arg Lys Thr Val Val Asn Phe Pro
                885                 890                 895

Val Glu Asp Glu Ala Leu Gly Gly Thr Ala Phe Val Gln Met Pro Ala
            900                 905                 910

His Gly Leu Phe Pro Trp Cys Gly Leu Leu Leu Asp Thr Arg Thr Leu
        915                 920                 925

Glu Val Gln Ser Asp Tyr Ser Ser Tyr Ala Arg Thr Ser Ile Arg Ala
    930                 935                 940

Ser Leu Thr Phe Asn Arg Gly Phe Lys Ala Gly Arg Asn Met Arg Arg
945                 950                 955                 960

Lys Leu Phe Gly Val Leu Arg Leu Lys Cys His Ser Leu Phe Leu Asp
                965                 970                 975

Leu Gln Val Asn Ser Leu Gln Thr Val Cys Thr Asn Ile Tyr Lys Ile
            980                 985                 990

Leu Leu Leu Gln Ala Tyr Arg Phe His Ala Cys Val Leu Gln Leu Pro
        995                 1000                1005

Phe His Gln Gln Val Trp Lys Asn Pro Thr Phe Phe Leu Arg Val Ile
    1010                1015                1020

Ser Asp Thr Ala Ser Leu Cys Tyr Ser Ile Leu Lys Ala Lys Asn Ala
1025                1030                1035                1040

Gly Met Ser Leu Gly Ala Lys Gly Ala Ala Gly Pro Leu Pro Ser Glu
```

```
                 1045              1050              1055
Ala Val Gln Trp Leu Cys His Gln Ala Phe Leu Leu Lys Leu Thr Arg
             1060              1065              1070

His Arg Val Thr Tyr Val Pro Leu Leu Gly Ser Leu Arg Thr Ala Gln
         1075              1080              1085

Thr Gln Leu Ser Arg Lys Leu Pro Gly Thr Thr Leu Thr Ala Leu Glu
     1090              1095              1100

Ala Ala Ala Asn Pro Ala Leu Pro Ser Asp Phe Lys Thr Ile Leu Asp
1105              1110              1115              1120

<210> SEQ ID NO 5
<211> LENGTH: 3426
<212> TYPE: DNA
<213> ORGANISM: Mus musculus

<400> SEQUENCE: 5
```

| | | | | | |
|---|---|---|---|---|---|
| gtgggaggcc | catcccggcc | ttgagcacaa | tgacccgcgc | tcctcgttgc | cccgcggtgc | 60 |
| gctctctgct | gcgcagccga | taccgggagg | tgtggccgcg | gcaacccttt | gtgcggcgcc | 120 |
| tggggcccga | gggcaggcgg | cttgtgcaac | ccggggaccc | gaagatctac | cgcactttgg | 180 |
| ttgcccaatg | cctagtgtgc | atgcactggg | gctcacagcc | tccacctgcc | gacctttcct | 240 |
| tccaccaggt | gtcatccctg | aaagagctgg | tggccagggt | gtgcagaga | ctctgcgagc | 300 |
| gcaacgagag | aaacgtgctg | gcttttggct | ttgagctgct | taacgaggcc | agaggcgggc | 360 |
| ctcccatggc | cttcactagt | agcgtgcgta | gctacttgcc | caacactgtt | attgagaccc | 420 |
| tgcgtgtcag | tggtgcatgg | atgctactgt | tgagccgagt | gggcgacgac | ctgctggtct | 480 |
| acctgctggc | acactgtgct | ctttatcttc | tggtgccccc | cagctgtgcc | taccaggtgt | 540 |
| gtgggtctcc | cctgtaccaa | atttgtgcca | ccacggatat | ctggccctct | gtgtccgcta | 600 |
| gttacaggcc | cacccgaccc | gtgggcagga | atttcactaa | ccttaggttc | ttacaacaga | 660 |
| tcaagagcag | tagtcgccag | gaagcaccga | aaccccctggc | cttgccatct | cgaggtacaa | 720 |
| agaggcatct | gagtctcacc | agtacaagtg | tgccttcagc | taagaaggcc | agatgctatc | 780 |
| ctgtcccgag | agtggaggag | ggaccccaca | ggcaggtgct | accaacccca | tcaggcaaat | 840 |
| catgggtgcc | aagtcctgct | cggtcccccg | aggtgcctac | tgcagagaaa | gatttgtctt | 900 |
| ctaaaggaaa | ggtgtctgac | ctgagtctct | ctgggtcggt | gtgctgtaaa | cacaagccca | 960 |
| gctccacatc | tctgctgtca | ccaccccgcc | aaaatgcctt | tcagctcagg | ccatttattg | 1020 |
| agaccagaca | tttcctttac | tccaggggag | atggccaaga | gcgtctaaac | ccctcattcc | 1080 |
| tactcagcaa | cctccagcct | aacttgactg | gggccaggag | actggtggag | atcatctttc | 1140 |
| tgggctcaag | gcctaggaca | tcaggaccac | tctgcaggac | acaccgtcta | tcgcgtcgat | 1200 |
| actggcagat | gcggcccctg | ttccaacagc | tgctggtgaa | ccatgcagag | tgccaatatg | 1260 |
| tcagactcct | caggtcacat | tgcaggtttc | gaacagcaaa | ccaacaggtg | acagatgcct | 1320 |
| tgaacaccag | cccaccgcac | ctcatggatt | tgctccgcct | gcagcagcagt | ccctggcagg | 1380 |
| tatatggttt | tcttcgggcc | tgtctctgca | aggtggtgtc | tgctagtctc | tggggtacca | 1440 |
| ggcacaatga | gcgccgcttc | tttaagaact | taaagaagtt | catctcgttg | gggaaatacg | 1500 |
| gcaagctatc | actgcaggaa | ctgatgtgga | agatgaaagt | agaggattgc | cactggctcc | 1560 |
| gcagcagccc | ggggaaggac | cgtgtccccg | ctgcagagca | ccgtctgagg | gagaggatcc | 1620 |
| tggctacgtt | cctgttctgg | ctgatggaca | catacgtggt | acagctgctt | aggtcattct | 1680 |
| tttacatcac | agagagcaca | ttccagaaga | acaggctctt | cttctaccgt | aagagtgtgt | 1740 |

```
ggagcaagct gcagagcatt ggagtcaggc aacaccttga gagagtgcgg ctacgggagc      1800
tgtcacaaga ggaggtcagg catcaccagg acacctggct agccatgccc atctgcagac      1860
tgcgcttcat ccccaagccc aacggcctgc ggccccattgt gaacatgagt tatagcatgg     1920
gtaccagagc tttgggcaga aggaagcagg cccagcattt cacccagcgt ctcaagactc      1980
tcttcagcat gctcaactat gagcggacaa acatcctca ccttatgggg tcttctgtac       2040
tgggtatgaa tgacatctac aggacctggc gggccttttgt gctgcgtgtg cgtgctctgg    2100
accagacacc caggatgtac tttgttaagg cagatgtgac cggggcctat gatgccatcc      2160
cccagggtaa gctggtggag gttgttgcca atatgatcag gcactcggag agcacgtact     2220
gtatccgcca gtatgcagtg gtccggagag atagccaagg ccaagtccac aagtccttta    2280
ggagacaggt caccaccctc tctgacctcc agccatacat gggccagttc cttaagcatc     2340
tgcaggattc agatgccagt gcactgagga actccgttgt catcgagcag agcatctcta    2400
tgaatgagag cagcagcagc ctgtttgact tcttcctgca cttcctgcgt cacagtgtcg     2460
taaagattgg tgacaggtgc tatacgcagt gccagggcat cccccagggc tccagcctat     2520
ccaccctgct ctgcagtctg tgtttcggag acatggagaa caagctgttt gctgaggtgc    2580
agcgggatgg gttgcttta cgttttgttg atgactttct gttggtgacg cctcacttgg      2640
accaagcaaa aaccttcctc agcacccctgg tccatgggcgt tcctgagtat gggtgcatga  2700
taaacttgca gaagacagtg gtgaacttcc ctgtggagcc tggtaccctg gtggtgcag     2760 ctccatacca gctgcctgct cactgcctgt ttccctggtg tggcttgctg ctggacactc     2820
agactttgga ggtgttctgt gactactcag gttatgccca gacctcaatt aagacgagcc    2880
tcaccttcca gagtgtcttc aaagctggga agaccatgcg gaacaagctc ctgtcggtct     2940
tgcggttgaa gtgtcacggt ctatttctag acttgcaggt gaacagcctc cagacagtct    3000
gcatcaatat atacaagatc ttcctgcttc aggcctacag gttccatgca tgtgtgattc     3060
agcttccctt tgaccagcgt gttaggaaga acctcacatt ctttctgggc atcatctcca    3120
gccaagcatc ctgctgctat gctatcctga aggtcaagaa tccaggaatg acactaaagg   3180
cctctggctc cttttcctcct gaagccgcac attggctctg ctaccaggcc ttcctgctca    3240
agctggctgc tcattctgtc atctacaaat gtctcctggg acctctgagg acagcccaaa    3300
aactgctgtg ccggaagctc ccagaggcga caatgaccat ccttaaagct gcagctgacc   3360 cagcccctaag cacagacttt cagaccattt tggactaacc ctgtctcctt ccgctagatg   3420
aacatg                                                                3426
```

<210> SEQ ID NO 6
<211> LENGTH: 1122
<212> TYPE: PRT
<213> ORGANISM: Mus musculus

<400> SEQUENCE: 6

Met Thr Arg Ala Pro Arg Cys Pro Ala Val Arg Ser Leu Leu Arg Ser
1               5                   10                  15

Arg Tyr Arg Glu Val Trp Pro Leu Ala Thr Phe Val Arg Arg Leu Gly
            20                  25                  30

Pro Glu Gly Arg Arg Leu Val Gln Pro Gly Asp Pro Lys Ile Tyr Arg
        35                  40                  45

Thr Leu Val Ala Gln Cys Leu Val Cys Met His Trp Gly Ser Gln Pro
    50                  55                  60

-continued

```
Pro Pro Ala Asp Leu Ser Phe His Gln Val Ser Leu Lys Glu Leu
 65                  70                  75                  80

Val Ala Arg Val Val Gln Arg Leu Cys Glu Arg Asn Glu Arg Asn Val
                 85                  90                  95

Leu Ala Phe Gly Phe Glu Leu Leu Asn Glu Ala Arg Gly Gly Pro Pro
            100                 105                 110

Met Ala Phe Thr Ser Ser Val Arg Ser Tyr Leu Pro Asn Thr Val Ile
            115                 120                 125

Glu Thr Leu Arg Val Ser Gly Ala Trp Met Leu Leu Leu Ser Arg Val
            130                 135                 140

Gly Asp Asp Leu Leu Val Tyr Leu Leu Ala His Cys Ala Leu Tyr Leu
145                 150                 155                 160

Leu Val Pro Pro Ser Cys Ala Tyr Gln Val Cys Gly Ser Pro Leu Tyr
                165                 170                 175

Gln Ile Cys Ala Thr Thr Asp Ile Trp Pro Ser Val Ser Ala Ser Tyr
            180                 185                 190

Arg Pro Thr Arg Pro Val Gly Arg Asn Phe Thr Asn Leu Arg Phe Leu
            195                 200                 205

Gln Gln Ile Lys Ser Ser Ser Arg Gln Glu Ala Pro Lys Pro Leu Ala
210                 215                 220

Leu Pro Ser Arg Gly Thr Lys Arg His Leu Ser Leu Thr Ser Thr Ser
225                 230                 235                 240

Val Pro Ser Ala Lys Lys Ala Arg Cys Tyr Pro Val Pro Arg Val Glu
                245                 250                 255

Glu Gly Pro His Arg Gln Val Leu Pro Thr Pro Ser Gly Lys Ser Trp
            260                 265                 270

Val Pro Ser Pro Ala Arg Ser Pro Glu Val Pro Thr Ala Glu Lys Asp
            275                 280                 285

Leu Ser Ser Lys Gly Lys Val Ser Asp Leu Ser Leu Ser Gly Ser Val
            290                 295                 300

Cys Cys Lys His Lys Pro Ser Ser Thr Ser Leu Leu Ser Pro Pro Arg
305                 310                 315                 320

Gln Asn Ala Phe Gln Leu Arg Pro Phe Ile Glu Thr Arg His Phe Leu
                325                 330                 335

Tyr Ser Arg Gly Asp Gly Gln Glu Arg Leu Asn Pro Ser Phe Leu Leu
            340                 345                 350

Ser Asn Leu Gln Pro Asn Leu Thr Gly Ala Arg Arg Leu Val Glu Ile
            355                 360                 365

Ile Phe Leu Gly Ser Arg Pro Arg Thr Ser Gly Pro Leu Cys Arg Thr
            370                 375                 380

His Arg Leu Ser Arg Arg Tyr Trp Gln Met Arg Pro Leu Phe Gln Gln
385                 390                 395                 400

Leu Leu Val Asn His Ala Glu Cys Gln Tyr Val Arg Leu Leu Arg Ser
                405                 410                 415

His Cys Arg Phe Arg Thr Ala Asn Gln Gln Val Thr Asp Ala Leu Asn
            420                 425                 430

Thr Ser Pro Pro His Leu Met Asp Leu Leu Arg Leu His Ser Ser Pro
            435                 440                 445

Trp Gln Val Tyr Gly Phe Leu Arg Ala Cys Leu Cys Lys Val Val Ser
            450                 455                 460

Ala Ser Leu Trp Gly Thr Arg His Asn Glu Arg Arg Phe Phe Lys Asn
465                 470                 475                 480

Leu Lys Lys Phe Ile Ser Leu Gly Lys Tyr Gly Lys Leu Ser Leu Gln
```

```
                485                 490                 495
Glu Leu Met Trp Lys Met Lys Val Glu Asp Cys His Trp Leu Arg Ser
                500                 505                 510

Ser Pro Gly Lys Asp Arg Val Pro Ala Ala Glu His Arg Leu Arg Glu
                515                 520                 525

Arg Ile Leu Ala Thr Phe Leu Phe Trp Leu Met Asp Thr Tyr Val Val
                530                 535                 540

Gln Leu Leu Arg Ser Phe Phe Tyr Ile Thr Glu Ser Thr Phe Gln Lys
545                 550                 555                 560

Asn Arg Leu Phe Phe Tyr Arg Lys Ser Val Trp Ser Lys Leu Gln Ser
                565                 570                 575

Ile Gly Val Arg Gln His Leu Glu Arg Val Arg Leu Arg Glu Leu Ser
                580                 585                 590

Gln Glu Glu Val Arg His His Gln Asp Thr Trp Leu Ala Met Pro Ile
                595                 600                 605

Cys Arg Leu Arg Phe Ile Pro Lys Pro Asn Gly Leu Arg Pro Ile Val
                610                 615                 620

Asn Met Ser Tyr Ser Met Gly Thr Arg Ala Leu Gly Arg Arg Lys Gln
625                 630                 635                 640

Ala Gln His Phe Thr Gln Arg Leu Lys Thr Leu Phe Ser Met Leu Asn
                645                 650                 655

Tyr Glu Arg Thr Lys His Pro His Leu Met Gly Ser Ser Val Leu Gly
                660                 665                 670

Met Asn Asp Ile Tyr Arg Thr Trp Arg Ala Phe Val Leu Arg Val Arg
                675                 680                 685

Ala Leu Asp Gln Thr Pro Arg Met Tyr Phe Val Lys Ala Asp Val Thr
                690                 695                 700

Gly Ala Tyr Asp Ala Ile Pro Gln Gly Lys Leu Val Glu Val Val Ala
705                 710                 715                 720

Asn Met Ile Arg His Ser Glu Ser Thr Tyr Cys Ile Arg Gln Tyr Ala
                725                 730                 735

Val Val Arg Arg Asp Ser Gln Gly Gln Val His Lys Ser Phe Arg Arg
                740                 745                 750

Gln Val Thr Thr Leu Ser Asp Leu Gln Pro Tyr Met Gly Gln Phe Leu
                755                 760                 765

Lys His Leu Gln Asp Ser Asp Ala Ser Ala Leu Arg Asn Ser Val Val
770                 775                 780

Ile Glu Gln Ser Ile Ser Met Asn Glu Ser Ser Ser Leu Phe Asp
785                 790                 795                 800

Phe Phe Leu His Phe Leu Arg His Ser Val Val Lys Ile Gly Asp Arg
                805                 810                 815

Cys Tyr Thr Gln Cys Gln Gly Ile Pro Gln Gly Ser Ser Leu Ser Thr
                820                 825                 830

Leu Leu Cys Ser Leu Cys Phe Gly Asp Met Glu Asn Lys Leu Phe Ala
                835                 840                 845

Glu Val Gln Arg Asp Gly Leu Leu Leu Arg Phe Val Asp Asp Phe Leu
                850                 855                 860

Leu Val Thr Pro His Leu Asp Gln Ala Lys Thr Phe Leu Ser Thr Leu
865                 870                 875                 880

Val His Gly Val Pro Glu Tyr Gly Cys Met Ile Asn Leu Gln Lys Thr
                885                 890                 895

Val Val Asn Phe Pro Val Glu Pro Gly Thr Leu Gly Gly Ala Ala Pro
                900                 905                 910
```

-continued

```
Tyr Gln Leu Pro Ala His Cys Leu Phe Pro Trp Cys Gly Leu Leu Leu
        915                 920                 925

Asp Thr Gln Thr Leu Glu Val Phe Cys Asp Tyr Ser Gly Tyr Ala Gln
    930                 935                 940

Thr Ser Ile Lys Thr Ser Leu Thr Phe Gln Ser Val Phe Lys Ala Gly
945                 950                 955                 960

Lys Thr Met Arg Asn Lys Leu Leu Ser Val Leu Arg Leu Lys Cys His
                965                 970                 975

Gly Leu Phe Leu Asp Leu Gln Val Asn Ser Leu Gln Thr Val Cys Ile
            980                 985                 990

Asn Ile Tyr Lys Ile Phe Leu Leu Gln Ala Tyr Arg Phe His Ala Cys
        995                 1000                1005

Val Ile Gln Leu Pro Phe Asp Gln Arg Val Arg Lys Asn Leu Thr Phe
    1010                1015                1020

Phe Leu Gly Ile Ile Ser Ser Gln Ala Ser Cys Cys Tyr Ala Ile Leu
1025                1030                1035                1040

Lys Val Lys Asn Pro Gly Met Thr Leu Lys Ala Ser Gly Ser Phe Pro
                1045                1050                1055

Pro Glu Ala Ala His Trp Leu Cys Tyr Gln Ala Phe Leu Leu Lys Leu
            1060                1065                1070

Ala Ala His Ser Val Ile Tyr Lys Cys Leu Leu Gly Pro Leu Arg Thr
        1075                1080                1085

Ala Gln Lys Leu Leu Cys Arg Lys Leu Pro Glu Ala Thr Met Thr Ile
    1090                1095                1100

Leu Lys Ala Ala Ala Asp Pro Ala Leu Ser Thr Asp Phe Gln Thr Ile
1105                1110                1115                1120

Leu Asp

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
ggcaccacac cttctacaat g                                          21

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
gtggtggtga agctgtag                                              18

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
ggattgccac tggctccg                                              18
```

```
<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tgcctgacct cctcttgtga c                                            21

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
gtggcttgtg ggaaaatagt tga                                          23

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ctggcttgat gatctgcctt tac                                          23

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
ccaatgagta ccgcgtgaa                                               19

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
acagtcatgc cgggatgat                                               19

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
ccctcggccc aagatccta                                               19

<210> SEQ ID NO 16
<211> LENGTH: 22
<212> TYPE: DNA
<213> ORGANISM: Artificial Sequence
<220> FEATURE:
<223> OTHER INFORMATION: Primer
```

```
<400> SEQUENCE: 16
ccacaggcat tccagagtca tc                                    22

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
ggaggacgtg gctgaagac                                        19

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
ggagcttgat gcccccaat                                        19

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
gagactggct attgggggag                                       20

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
gaccgaaatg cttccaggg                                        19

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
caactatcgg ccaactcatt ga                                    22

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
gcagttcttc ataagcggag at                                    22
```